United States Patent
Kamon

(10) Patent No.: US 11,103,197 B2
(45) Date of Patent: Aug. 31, 2021

(54) DIAGNOSIS SUPPORT SYSTEM, ENDOSCOPE SYSTEM, PROCESSOR AND DIAGNOSIS SUPPORT METHOD

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/783,138

(22) Filed: Feb. 5, 2020

(65) Prior Publication Data

US 2020/0170484 A1     Jun. 4, 2020

Related U.S. Application Data

(63) Continuation of application No. PCT/JP2018/029489, filed on Aug. 6, 2018.

(30) Foreign Application Priority Data

Aug. 25, 2017    (JP) .............................. JP2017-162546

(51) Int. Cl.
     *A61B 5/00*          (2006.01)
     *A61B 1/00*          (2006.01)
     (Continued)

(52) U.S. Cl.
     CPC .......... *A61B 5/7425* (2013.01); *A61B 1/0005* (2013.01); *A61B 1/005* (2013.01);
     (Continued)

(58) Field of Classification Search
     CPC ....... A61B 5/742; A61B 5/7425; A61B 5/748; A61B 5/7485
     See application file for complete search history.

(56) References Cited

U.S. PATENT DOCUMENTS

2010/0067808 A1    3/2010    Matsuzaki
2010/0097392 A1    4/2010    Nishiyama et al.
(Continued)

FOREIGN PATENT DOCUMENTS

JP      S60203077      10/1985
JP      2001359039     12/2001
(Continued)

OTHER PUBLICATIONS

A. Sieg, "Capsule endoscopy compared with conventional colonoscopy for detection of colorectal neoplasms", 3 World J. Gastrointestinal Endosclopy 81-85 (May 16, 2011) (Year: 2011).*

(Continued)

*Primary Examiner* — David N Werner
(74) *Attorney, Agent, or Firm* — JCIPRNET

(57) ABSTRACT

A diagnosis support system having an image sensor that captures a medical image and a processor configured to capture medical images of which imaging times are different, store any of medical images as representative images, store the medical images excluding the representative images as groups of neighboring images such that each the groups of neighboring images are associated with the representative images, display the representative images in a list on a display device, receive a selection from the representative images displayed in the list, extract a neighboring image for diagnosis from among a group of neighboring images which is associated with a selected representative image, and display the extracted neighboring image for diagnosis on the display.

17 Claims, 22 Drawing Sheets

(51) Int. Cl.
    *A61B 1/005*     (2006.01)
    *A61B 1/045*     (2006.01)
    *H04N 5/232*     (2006.01)
    *H04N 7/18*     (2006.01)

(52) U.S. Cl.
    CPC ...... *A61B 1/00009* (2013.01); *A61B 1/00096* (2013.01); *A61B 1/045* (2013.01); *A61B 5/742* (2013.01); *A61B 5/748* (2013.01); *A61B 5/7485* (2013.01); *H04N 5/23216* (2013.01); *H04N 7/183* (2013.01); *H04N 7/188* (2013.01)

(56) References Cited

U.S. PATENT DOCUMENTS

| | | | | |
|---|---|---|---|---|
| 2013/0315455 | A1* | 11/2013 | Wakai | A61B 8/5215 |
| | | | | 382/128 |
| 2016/0133037 | A1* | 5/2016 | Vemulapalli | G06T 11/60 |
| | | | | 382/128 |
| 2018/0098740 | A1* | 4/2018 | Brunner | G16H 30/20 |

FOREIGN PATENT DOCUMENTS

| | | |
|---|---|---|
| JP | 2008061704 | 3/2008 |
| JP | 2009077765 | 4/2009 |
| JP | 2009211118 | 9/2009 |
| JP | 2010094185 | 4/2010 |
| JP | 2010172673 | 8/2010 |
| JP | 2011156203 | 8/2011 |
| JP | 2011200283 | 10/2011 |
| JP | 2012249936 | 12/2012 |
| JP | 2013017755 | 1/2013 |
| JP | 2013128723 | 7/2013 |
| JP | 2014053723 | 3/2014 |
| WO | 2008155974 | 12/2008 |

OTHER PUBLICATIONS

"International Search Report (Form PCT/ISA/210)" of PCT/JP2018/029489, dated Oct. 23, 2020, with English translation thereof, pp. 1-3.

"International Preliminary Report on Patentability (Form PCT/IPEA/409) of PCT/JP2018/029489," completed on Nov. 1, 2019, with English translation thereof, pp. 1-21.

"Office Action of Japan Counterpart Application", dated Oct. 27, 2020, with English translation thereof, p. 1-p. 10.

"Office Action of Japan Counterpart Application", dated Feb. 8, 2021, with English translation thereof, pp. 1-15.

\* cited by examiner

- 207
  - REPRESENTATIVE IMAGE — 207A
  - NEIGHBORING IMAGE — 207B
  - DESIGNATED IMAGE — 207C

| REPRESENTATIVE IMAGE | NEIGHBORING IMAGE |
|---|---|
| i101 | i102 TO i111 |
| i201 | i202 TO i211 |
| ⋮ | ⋮ |
| i901 | i902 TO i911 |
| ⋮ | ⋮ |

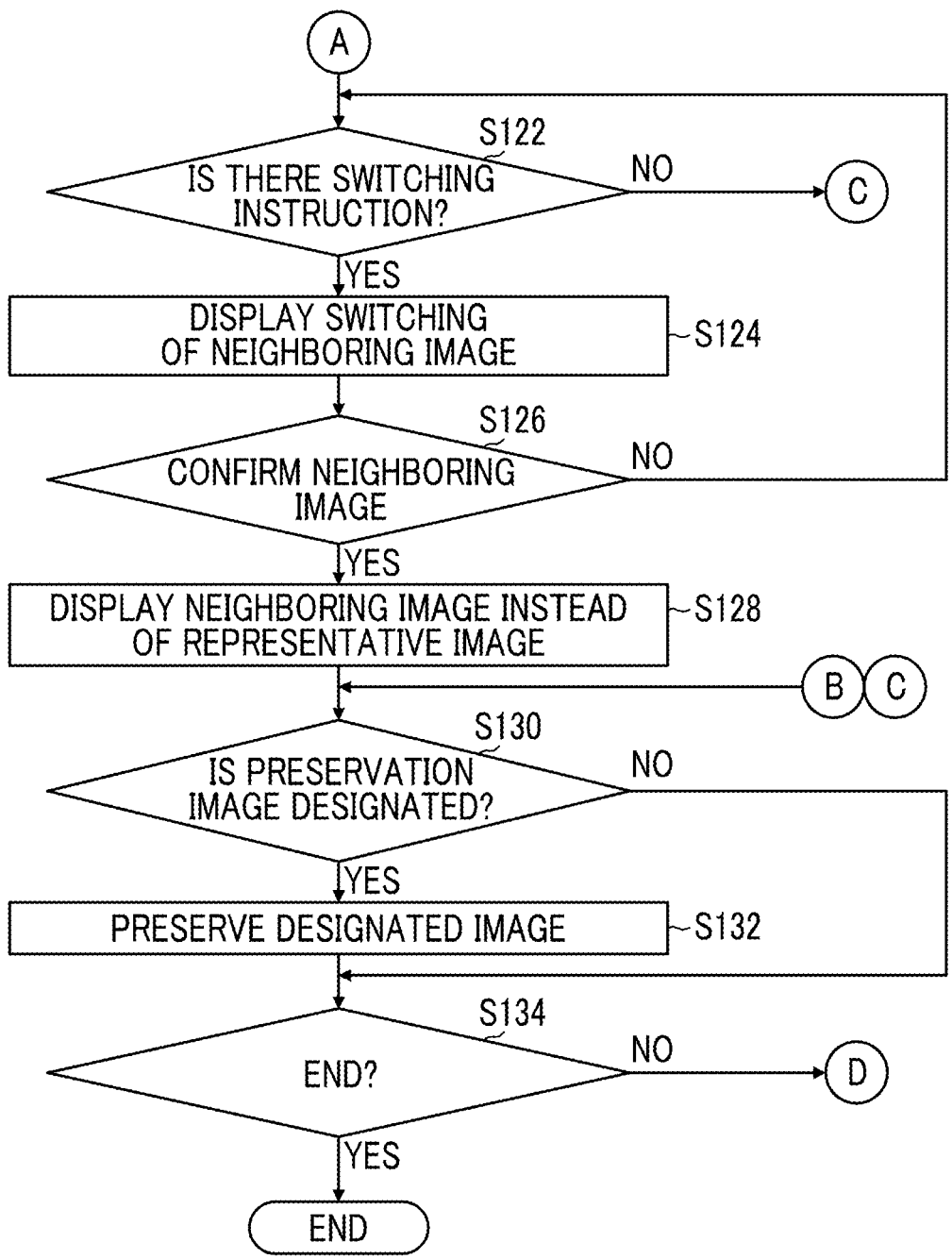

FIG. 9

| C01 NUMBER OF IMAGES TO BE ACQUIRED THROUGH SINGLE-SHOT IMAGING | V01 10 IMAGES | A01 ▼ |
|---|---|---|
| C02 IMAGING PERIOD | V02 10 SECONDS | A02 ▼ |
| C03 REPRESENTATIVE IMAGE | V03 FIRST IMAGE | A03 ▼ |
| C04 DETECT REGION OF INTEREST | V04 ON | A04 ▼ |
| C05 AUTOMATICALLY IMAGING IN CASE WHERE REGION OF INTEREST HAS BEEN DETECTED | V05 ON | A05 ▼ |
| C06 DETECT INSTRUMENT OR THE LIKE | V06 ON | A06 ▼ |
| C07 AUTOMATICALLY IMAGING IN CASE WHERE AN INSTRUMENT OR THE LIKE HAS BEEN DETECTED | V07 ON | A07 ▼ |
| C08 DETECT A PIGMENT AGENT OR THE LIKE | V08 ON | A08 ▼ |
| C09 AUTOMATICALLY IMAGING IN CASE WHERE PIGMENT AGENT OR THE LIKE HAS BEEN DETECTED | V09 ON | A09 ▼ |
| C10 AUTOMATICALLY EXTRACT DIAGNOSIS NEIGHBORING IMAGE | V10 ON | A10 ▼ |
| C10a AUTOMATICALLY EXTRACTING CONDITION OF DIAGNOSIS NEIGHBORING IMAGE | V10a EXPOSURE | A10a ▼ |

B01 OK   B02 CANCEL   B03 INITIAL SETTING

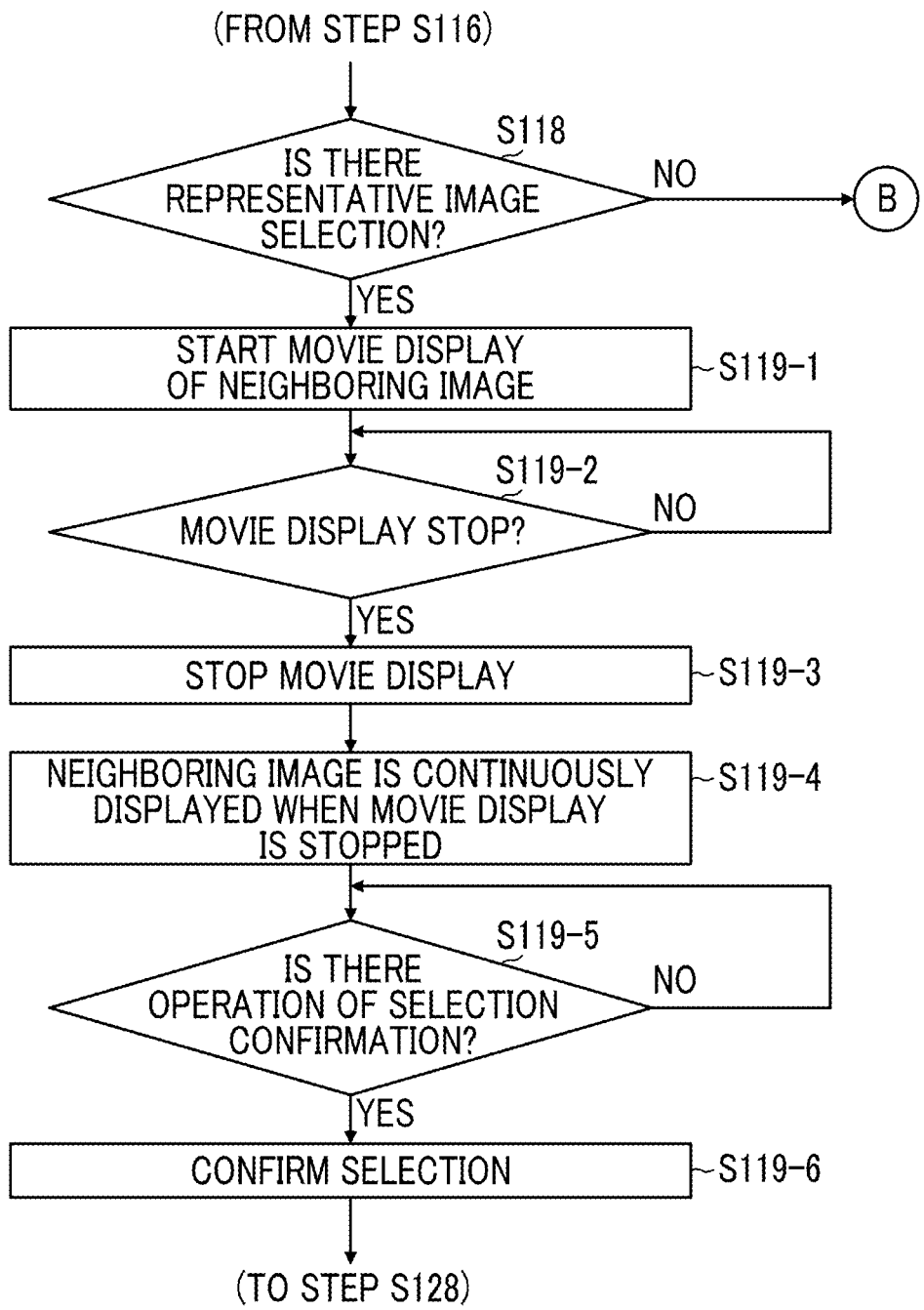

DIAGNOSIS SUPPORT SYSTEM, ENDOSCOPE SYSTEM, PROCESSOR AND DIAGNOSIS SUPPORT METHOD

CROSS-REFERENCE TO RELATED APPLICATIONS

This application is a Continuation of PCT International Application No. PCT/JP2018/029489 filed on Aug. 6, 2018, which claims priority under 35 U.S.C § 119(a) to Japanese Patent Application No. 2017-162546 filed on Aug. 25, 2017. Each of the above applications is hereby expressly incorporated by reference, in its entirety, into the present application.

BACKGROUND OF THE INVENTION

1. Field of the Invention

The present invention relates to a diagnosis support system, an endoscope system, a processor, and a diagnosis support method, and particularly to acquisition and display of an medical image.

2. Description of the Related Art

In diagnosis using medical equipment, an image of an object to be examined (patient or the like) is acquired and diagnosis is performed on the basis of the acquired image. In such diagnosis using the medical image, a plurality of images are acquired and displayed in many cases, and thus a system capable of displaying an image suitable for diagnosis is desired.

Regarding a system of acquiring and displaying an medical image, for example, JP2013-017755A discloses that images acquired by a plurality of modalities are displayed in a list, and a display period for electrocardiogram waveforms is switched on the basis of observation data and behavior information to display a partial image. Specifically, it is disclosed that in a case where a user operates a keyboard of an interpretation terminal in a state where an n-th electrocardiogram image is displayed among images for which the observation information is "tachycardia", a partial image with an (n−1)-th or (n+1)-th "tachycardia" is displayed.

SUMMARY OF THE INVENTION

In some cases, instantaneous defects such as shaking or blur occur in a case where an medical image is captured so that an appropriate image cannot be displayed to cause hindrance in diagnosis. Such a problem becomes remarkable in a situation where a large number of images are displayed for diagnosis. Regarding such a problem, in JP2013-017755A, partial images with the electrocardiogram waveforms of which the display periods are different are switched, but it does not mean that an image with inappropriate waveforms is switched to an image with appropriate waveforms. JP2013-017755A does not disclose countermeasures for a case where there is an inappropriate image, for images such as computed tomography (CT), or magnetic resonance imaging (MM). In the related art, an image suitable for diagnosis cannot be easily displayed, and thus, diagnosis, report creation, and the like cannot be performed efficiently.

The invention has been made in consideration of the above-described circumstances, and an object of the invention is to provide a diagnosis support system, an endoscope system, a processor, and a diagnosis support method which can easily display an image suitable for diagnosis.

In order to achieve the above-described object, a diagnosis support system according to a first aspect of the invention comprises a diagnosis support system comprising: an image sensor that captures a medical image according to an imaging instruction; and a processor configured to: issue the imaging instruction to the image sensor to capture a plurality of medical images of which imaging times are different; store any of the plurality of medical images as representative images; store the plurality of medical images excluding the representative images as a plurality of groups of neighboring images such that each the plurality of groups of neighboring images are associated with the representative images; display the representative images in a list on a display device; receive a selection from the representative images displayed in the list; extract a neighboring image for diagnosis, from among a group of neighboring images which is associated with a selected representative image, by analyzing the neighboring images on the basis of at least one of exposures when the image sensor captures the neighboring images, or shaking amounts when the image sensor captures the neighboring images; and display the extracted neighboring image for diagnosis on the display.

According to the first aspect, a neighboring image with few shaking or blur may be displayed in a case where the representative image is defective due to an instantaneous cause such as shaking or blur. In this manner, it is possible to easily display an image suitable for diagnosis and to perform diagnosis, report creation, and the like.

In the first aspect, the representative image may be any of the acquired images (the imaging time is the earliest, the latest, the middle, and the like among the plurality of images). Further, the representative images may be displayed in a list by being arranged in consideration of an imaging time, an imaged part, a region of interest, an instrument and/or equipment used, a pigment and/or a dye used, and the like.

In the first aspect and the respective aspects to be described below, an image for medical use is referred to as a medical image. As a light source used for capturing an medical image, a light source that generates light in a white-light wavelength range or light in a plurality of wavelength ranges (narrow-band light) as the white-light wavelength range, infrared light, and excitation light can be used. Further, the medical image acquired in the first aspect may be a normal light image obtained from the application of light in a white-light wavelength range or light in a plurality of wavelength ranges as the light in a white-light wavelength range, or may be a special light image including information about the specific wavelength range on the basis of the normal light image.

BRIEF DESCRIPTION OF THE DRAWINGS

FIG. 8 is another flowchart showing the processing of the diagnosis support method.

FIG. 9 is a diagram showing an example of an imaging condition setting screen.

FIG. 18 is a flowchart showing processing of the movie display of the neighboring images.

DESCRIPTION OF THE PREFERRED EMBODIMENTS

A diagnosis support system, an endoscope system, a processor, and a diagnosis support method according to embodiments of the invention will be described in detail below with reference to the accompanying drawings.

First Embodiment

Figure 1:
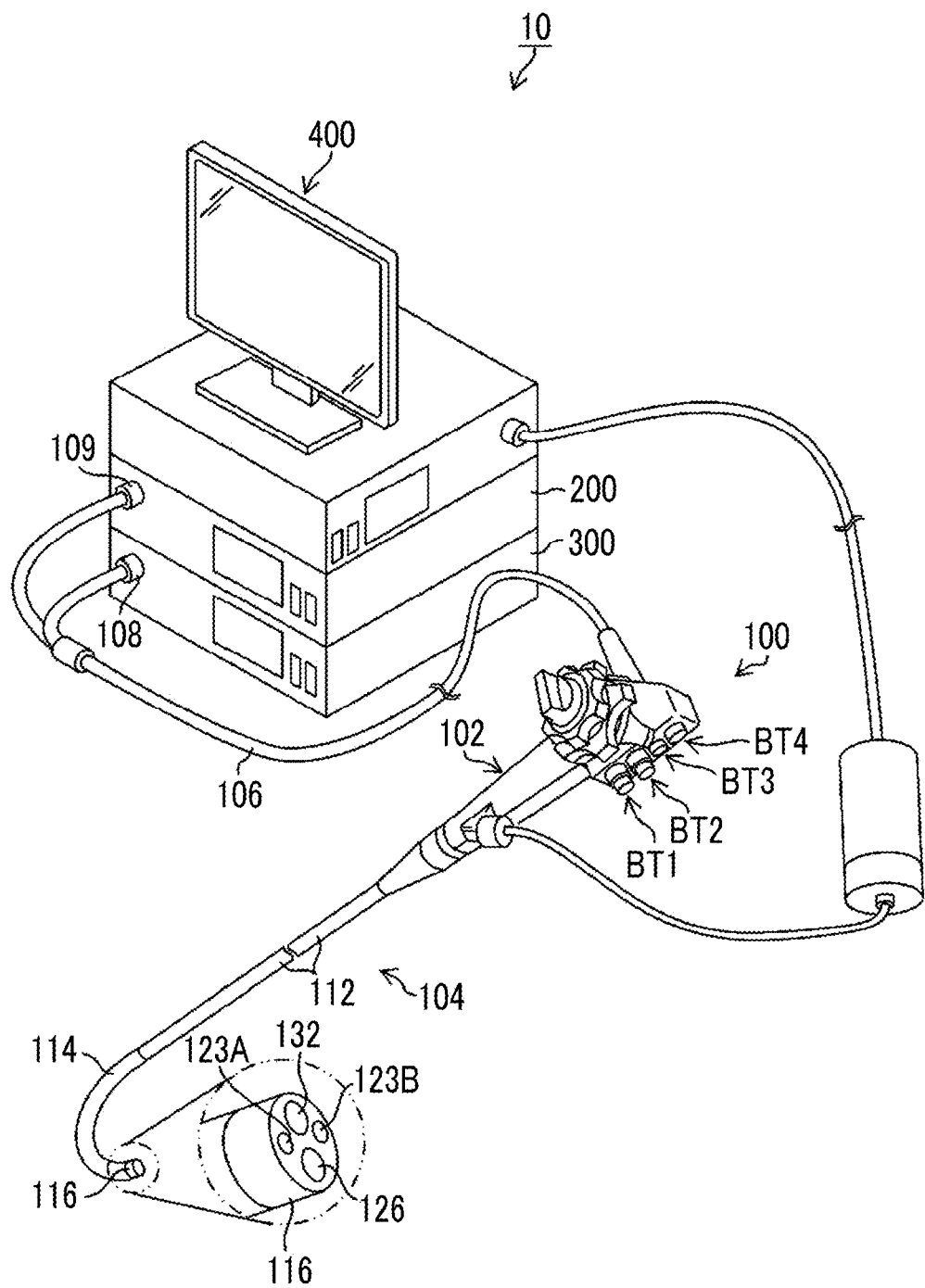
FIG. 1 is a diagram showing the appearance of an endoscope system according to an embodiment of the invention.
Figure 2:
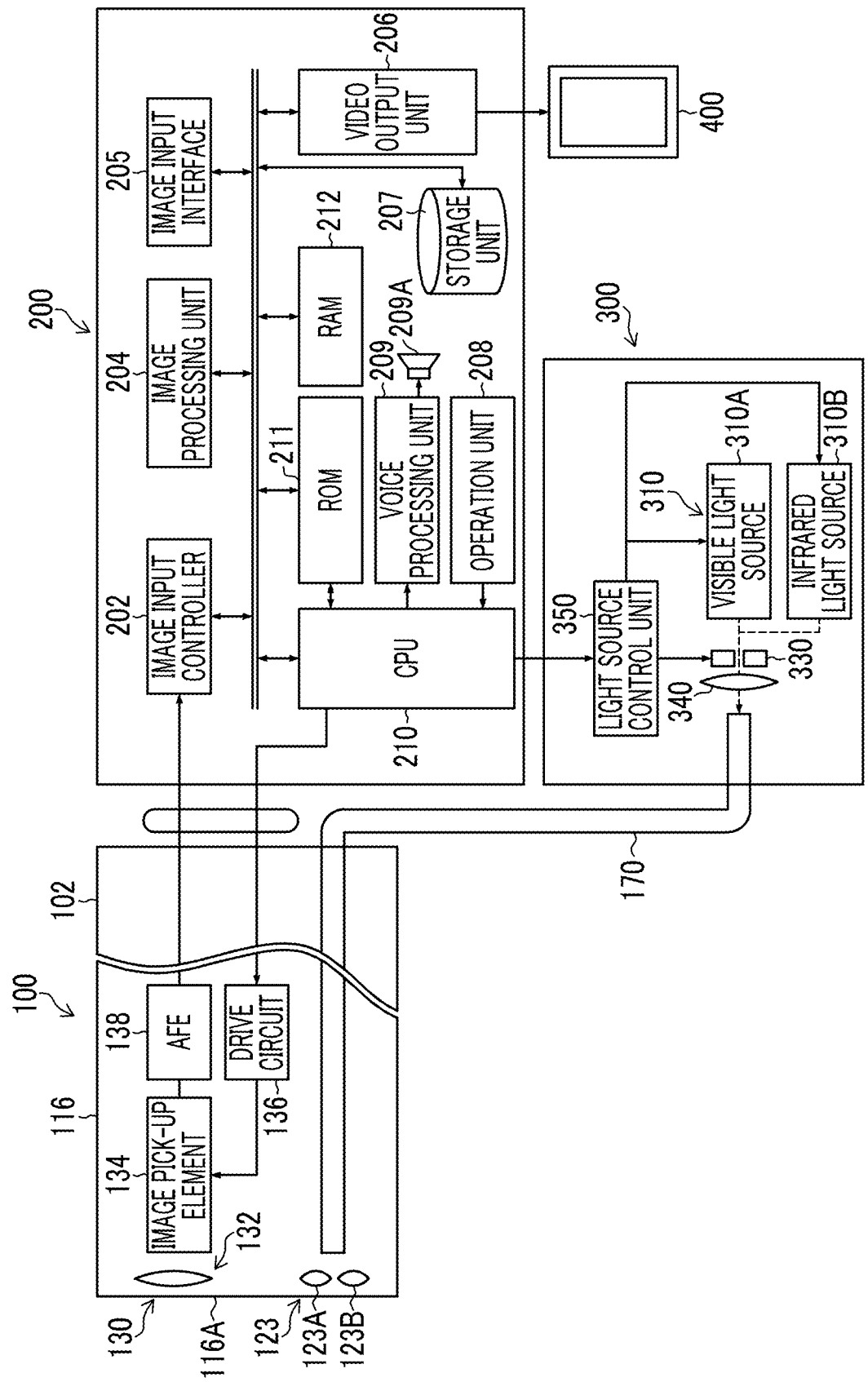
FIG. 2 is a block diagram showing the configuration of the endoscope system.

FIG. 1 is a diagram showing the appearance of an endoscope system 10 (diagnosis support system, diagnosis support apparatus, endoscope system, processor, medical image processing device) according to a first embodiment, and FIG. 2 is a block diagram showing the main configuration of the endoscope system 10. As shown in FIGS. 1 and 2, the endoscope system 10 includes an endoscope body 100 (endoscope), a processor 200 (processor, medical image processing device), a light source device 300, and a monitor 400 (display device).

<Configuration of Endoscope Body>

The endoscope body 100 comprises a hand operation part 102 (operation part) and an insertion part 104 (insertion part) connected to the hand operation part 102. An operator (user) grips and operates the hand operation part 102, inserts the insertion part 104 into an object to be examined (living body), and observes the object to be examined. Further, the hand operation part 102 is provided with an air/water supply button BT1, a suction button BT2, a function button BT3 to which various functions are assigned, and an imaging button BT4 that receives an imaging instruction operation. The insertion part 104 includes a soft portion 112 (soft portion), a bendable portion 114 (bendable portion), and a hard distal end portion 116 (hard distal end portion) that are arranged in this order from the hand operation part 102. That is, the bendable portion 114 is connected to the proximal end side of the hard distal end portion 116, and the soft portion 112 is connected to the proximal end side of the bendable portion 114. The hand operation part 102 is connected to the proximal end side of the insertion part 104. In a case where a user operates the hand operation part 102, the user can bend the bendable portion 114 to vertically and laterally change the direction of the hard distal end portion 116. The hard distal end portion 116 is provided with an imaging optical system 130 (image-for-medical-use capturing unit, imaging device, medical image acquisition unit), an illumination unit 123, a forceps port 126, and the like (refer to FIGS. 1 to 3).

At the time of observation and treatment, either visible light or infrared light, or both visible light and infrared light can be applied from illumination lenses 123A and 123B of the illumination unit 123 by the operation of an operation unit 208 (refer to FIG. 2). Further, cleaning water is ejected from a water supply nozzle (not shown) by the operation of the air/water supply button BT1, so that an imaging lens 132 (imaging lens) of the imaging optical system 130 and the illumination lenses 123A and 123B can be cleaned. A pipe line (not shown) communicates with the forceps port 126 that is opened at the hard distal end portion 116, and a treatment tool (not shown) for the removal of a tumor or the like is inserted into the pipe line and is appropriately moved forwards and backwards to perform necessary treatment on an object to be examined.

Figure 3:
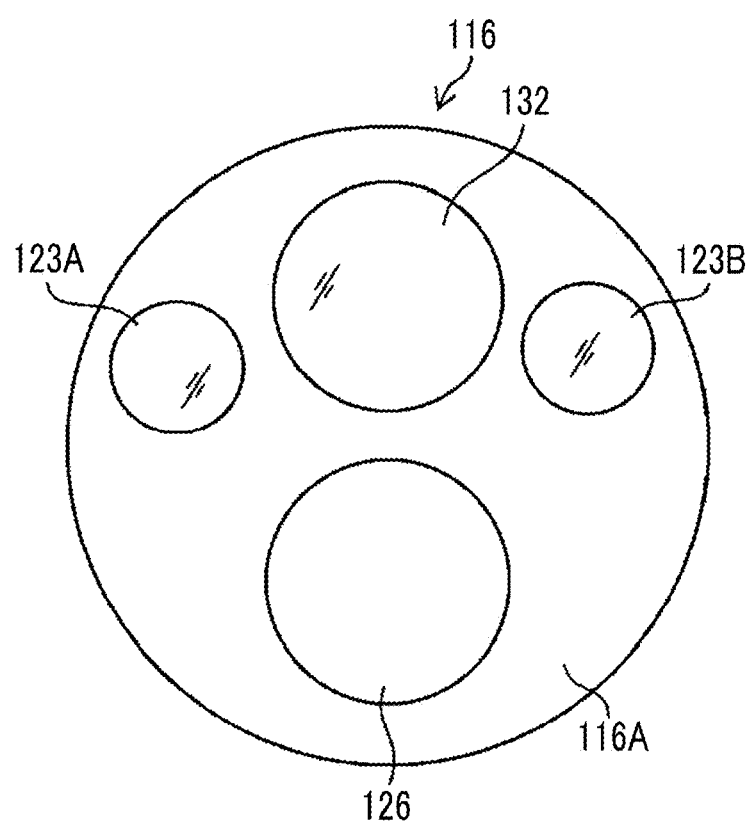
FIG. 3 is a diagram showing the configuration of a hard distal end portion of an endoscope.

As shown in FIGS. 1 to 3, the imaging lens 132 is provided on a distal end-side end face 116A of the hard distal end portion 116. A complementary-metal-oxide-semiconductor (CMOS) type image pick-up element 134 (image pick-up element, imaging device, medical image acquisition unit), a drive circuit 136, and an analog front end (AFE) 138 are provided in the back of the imaging lens 132, and image signals are output by these elements. The image pick-up element 134 is a color image pick-up element, and comprises a plurality of pixels formed of a plurality of light-receiving elements that are arranged in a matrix form (two-dimensionally arrayed) so as to have a specific pattern array (Bayer array, X-Trans (registered trademark) array, honeycomb array, or the like). Each pixel of the image pick-up element 134 includes a microlens, a red (R), green (G), or blue (B) color filter, and a photoelectric conversion part (photodiode or the like). The imaging optical system 130 also can generate a color image from pixel signals corresponding to three colors of red, green, and blue, and also can generate an image from pixel signals corresponding to any one color or two colors of red, green, and blue. A case where the image pick-up element 134 is a CMOS type image pick-up element has been described in the first embodiment, but the image pick-up element 134 may be a charge-coupled-device (CCD) type image pick-up element.

The optical image of an object to be examined (tumor area or lesion area) is formed on the light-receiving surface (image pick-up surface) of the image pick-up element 134 by the imaging lens 132 and is converted into electrical signals, and the electrical signals are output to the processor 200 through a signal cable (not shown) and are converted into video signals. Accordingly, an observation image (representative image, neighboring image) is displayed on the monitor 400 connected to the processor 200.

Further, the illumination lens 123A (for visible light) and the illumination lens 123B (for infrared light) of the illumination unit 123 are provided on the distal end-side end face 116A of the hard distal end portion 116 so as to be adjacent to the imaging lens 132. An emitting end of a light guide 170 to be described below is provided in the back of the illumination lenses 123A and 123B; the light guide 170 is inserted into the insertion part 104, the hand operation part 102, and a universal cable 106; and an incident end of the light guide 170 is disposed in a light guide connector 108.

<Configuration of Light Source Device>

As shown in FIG. 2, the light source device 300 includes a light source 310 for illumination, a stop 330, a condenser lens 340, a light source control unit 350, and the like, and causes illumination light (visible light or infrared light) to be incident on the light guide 170. The light source 310 comprises a visible light source 310A and an infrared light source 310B, and can apply either visible light or infrared light or both visible light and infrared light. The illuminance of illumination light applied by the visible light source 310A and the infrared light source 310B is controlled by the light source control unit 350, so that the illuminance of illumination light can be lowered or illumination can be stopped as necessary.

<Wavelength Range of Light Source>

The light source 310 (visible light source 310A) may be a light source that generates light in a white-light wavelength range or generates light in a plurality of wavelength ranges as light in a white-light wavelength range, and may be a light source that generates light in a specific wavelength range narrower than the white-light wavelength range. The specific wavelength range may be a blue-light wavelength range or a green-light wavelength range of a visible-light wavelength range or a red-light wavelength range of a visible-light wavelength range. In a case where the specific wavelength range is a blue-light wavelength range or a green-light wavelength range of a visible-light wavelength range, the specific wavelength range may include a wavelength range of 390 nm to 450 nm or 530 nm to 550 nm, and light in the specific wavelength range may have a peak wavelength in a wavelength range of 390 nm to 450 nm or 530 nm to 550 nm. Further, in a case where the specific wavelength range is a red-light wavelength range of a visible-light wavelength range, the specific wavelength range may include a wavelength range of 585 nm to 615 nm or 610 nm to 730 nm, and light in the specific wavelength range may have a peak wavelength in a wavelength range of 585 nm to 615 nm or 610 nm to 730 nm.

Light in the above-described specific wavelength range may include a wavelength range where a light absorption coefficient in oxyhemoglobin is different from that in reduced hemoglobin, and may have a peak wavelength in a wavelength range where a light absorption coefficient in oxyhemoglobin is different from that in reduced hemoglobin. In this case, the specific wavelength range may include a wavelength range of 400±10 nm, 440±10 nm, 470±10 nm, or 600 nm to 750 nm, and light in the specific wavelength may have a peak wavelength in a wavelength range of 400±10 nm, 440±10 nm, 470±10 nm, or 600 nm to 750 nm.

Further, light generated by the light source 310 (infrared light source 310B) may have a wavelength range of 790 nm to 820 nm or 905 nm to 970 nm, and may have a peak wavelength in a wavelength range of 790 nm to 820 nm or 905 nm to 970 nm.

Further, the light source 310 may comprise a light source that applies excitation light having a peak wavelength in a wavelength range of 390 nm to 470 nm. In this case, an medical image (in-vivo image), which includes information about the fluorescence of a fluorescent material present in an object to be examined (living body), can be acquired.

It is preferable that the type (laser light source, xenon light source, light-emitting-diode (LED) light source, and the like) and wavelength of the light source 310, the presence or absence of a filter, and the like are determined according to the type of a subject, the purpose of observation, and the like. Further, it is preferable that the wavelengths of illumination light are combined and/or switched according to the type of a subject, the purpose of observation, and the like at the time of observation. In a case where the wavelengths are to be switched, for example, a disc-shaped filter (rotary color filter) provided with filters, which are disposed in front of a light source and transmit or block light having specific wavelengths, may be rotated to switch the wavelength of light to be applied.

Furthermore, an image pick-up element, which is used to embody the invention, is not limited to a color image pick-up element where a color filter is provided for each pixel as with the image pick-up element 134, and may be a monochromatic image pick-up element. In a case where a monochromatic image pick-up element is used, image pick-up can be performed in order of surface (in order of color) while the wavelengths of illumination light are sequentially switched. For example, the wavelengths of illumination light to be emitted may be sequentially switched among purple, blue, green, and red; and broadband light (white light) may be applied and the wavelengths of illumination light to be emitted may be switched by the rotary color filter (red, green, blue, and the like). Moreover, one or a plurality of narrow-band lights (green light, blue light, and the like) may be applied and the wavelengths of illumination light to be emitted may be switched by the rotary color filter (green, blue, and the like). The narrow-band lights may be infrared lights having two or more different wavelengths.

The light guide connector 108 (refer to FIG. 1) is connected to the light source device 300, so that illumination light applied from the light source device 300 is transmitted to the illumination lenses 123A and 123B through the light guide 170 and is applied to an observation range from the illumination lenses 123A and 123B.

<Configuration of Processor>

The configuration of the processor 200 will be described with reference to FIG. 2. The image signals output from the endoscope body 100 are input to the processor 200 through an image input controller 202 and an image input interface 205, and the processor 200 performs necessary image processing on the image signals by an image processing unit 204 and outputs the resultant signals through a video output unit 206. Accordingly, an observation image (in-vivo images such as a representative image or a neighboring image) is displayed on the monitor 400 (display device). These kinds of processing are performed under the control of a central processing unit (CPU) 210. That is, the CPU 210 has functions as an image-for-medical-use capturing unit, an imaging control unit, a representative image storage unit, a neighboring image storage unit, a representative image display control unit, a representative image selection unit, a neighboring image display control unit, an imaging timing setting unit, a region-of-interest detection unit, an imaging instruction receiving unit, a switching instruction receiving unit, an image analysis unit, and a designated image preservation unit. As described below in detail, the image processing unit 204 performs setting, storage, switching of display, and the like of a representative image and/or a neighboring image. Images of a subject (representative image, neighboring image, and the like) are stored in a storage unit 207 (representative image storage unit, neighboring image storage unit). A voice processing unit 209 outputs warning messages (voice) or the like at the time of setting display conditions, from a speaker 209A by the control of the CPU 210 and the image processing unit 204.

Furthermore, a read only memory (ROM) 211 is a non-volatile storage element (non-temporary recording medium), and computer-readable codes of a program, which cause the CPU 210 and/or the image processing unit 204 to execute a diagnosis support method according to an embodiment of the invention, are stored in the ROM 211. A random access memory (RAM) 212 is a storage element for temporary storage at the time of various kinds of processing, and can also be used as a buffer at the time of acquisition of a neighboring image.

<Functions of Image Processing Unit>

Figure 4:
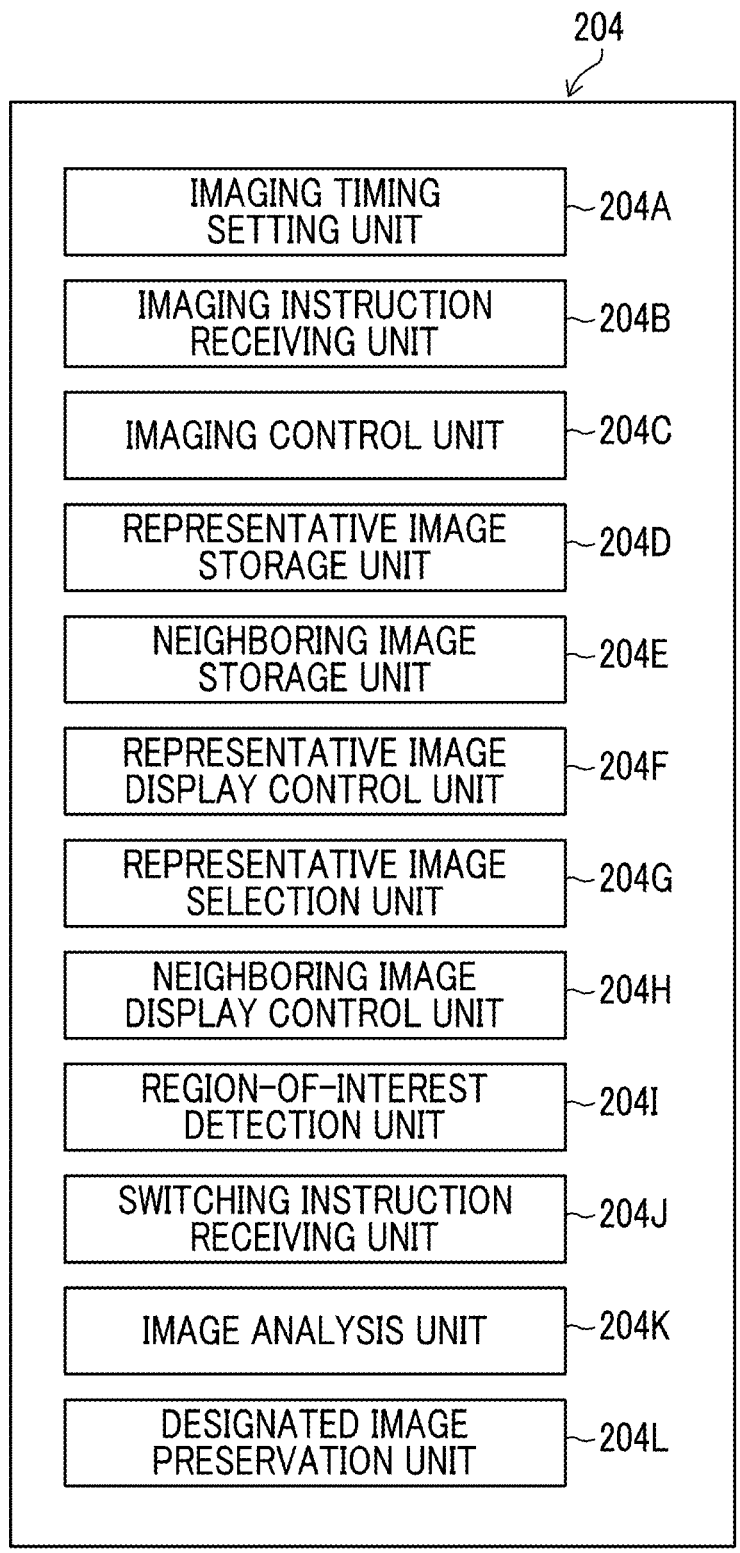
FIG. 4 is a diagram showing the functional configuration of an image processing unit.

FIG. 4 is a diagram showing the functional configuration of the image processing unit 204 (medical image acquisition unit, medical image analysis processing unit, medical image analysis result acquisition unit). The image processing unit 204 includes an imaging timing setting unit 204A, an imaging instruction receiving unit 204B, an imaging control unit 204C, a representative image storage unit 204D, a neighboring image storage unit 204E, a representative image display control unit 204F, a representative image selection unit 204G, a neighboring image display control unit 204H, a region-of-interest detection unit 204I, a switching instruction receiving unit 204J, an image analysis unit 204K, and a designated image preservation unit 204L. The imaging control unit 204C is operated as the medical image acquisition unit, and the region-of-interest detection unit 204I and the image analysis unit 204K are operated as the medical image analysis processing unit.

The image processing unit 204 may comprise a special-light-image acquisition unit that acquires a special light image including information about the specific wavelength range on the basis of a normal light image obtained from the application of light in a white-light wavelength range or light in a plurality of wavelength ranges as the light in a white-light wavelength range. In this case, a signal in the specific wavelength range can be obtained from an arithmetic operation based on color information about RGB (R: red, G: green, and B: blue) or CMY (C: cyan, M: magenta, and Y: yellow) included in the normal light image.

Further, the image processing unit 204 may comprise a feature-quantity-image generation unit generating a feature quantity image from an arithmetic operation based on at least one of a normal light image that is obtained from the application of light in a white-light wavelength range or light in a plurality of wavelength ranges as the light in a white-light wavelength range and a special light image that is obtained from the application of light in a specific wavelength range, and may acquire and display a feature quantity image as an image for medical use (medical image).

The processing to be fulfilled by these functions of the image processing unit 204 will be described in detail below. The processing to be fulfilled by these functions is performed under the control of the CPU 210.

The functions of the above-described image processing unit 204 can be fulfilled using various processors. The various processors include a central processing unit (CPU) that is a general-purpose processor fulfilling various functions by executing software (program), for example.

Further, the above-described various processors also include a programmable logic device (PLD) that is a processor of which the circuit configuration can be changed after manufacture, such as a field programmable gate array (FPGA). Furthermore, the above-described various processors also include dedicated electrical circuitry, which is a processor having a circuit configuration designed exclusively to execute specific processing, such as an application specific integrated circuit (ASIC).

The functions of each unit may be fulfilled by one processor, or may be fulfilled by a plurality of processors in combination. Further, a plurality of functions may be fulfilled by one processor. As an example where a plurality of functions are formed by one processor, first, there is an aspect where one processor is formed of a combination of one or more CPUs and software as typified by a computer, such as a client or a server, and this processor fulfills a plurality of functions. Second, there is an aspect where a processor fulfilling the functions of the entire system by one integrated circuit (IC) chip as typified by System On Chip (SoC) or the like is used. In this way, various functions are formed using one or more of the above-described various processors as hardware structures.

Furthermore, the hardware structures of these various processors are more specifically electrical circuitry where circuit elements, such as semiconductor elements, are combined.

In a case where the above-described processor (or electrical circuitry) is to execute software (program), computer-readable codes of the software to be executed (including the program for causing the diagnosis support method according to an embodiment of the invention to be executed) are stored in a non-temporary recording medium, such as the ROM 211 (refer to FIG. 2), and the processor refers to the software. In a case where processing is to be performed using software, for example, the RAM 212 (refer to FIG. 2) is used as a temporary storage region and the processor or electrical circuitry can also refer to data stored in, for example, an electronically erasable and programmable read only memory (EEPROM). In FIG. 4, illustration of devices such as the EEPROM and the like is omitted.

<Configuration of Operation Unit>

The processor 200 comprises the operation unit 208. The operation unit 208 comprises an operation mode setting switch (not shown) and the like, and can operate the application of visible light and/or infrared light. Further, the operation unit 208 includes a keyboard and a mouse (which are not shown), and a user can perform selection, a switching operation, and the like of the representative image and/or the neighboring image via the devices. Setting of the imaging condition and the display condition by the operation unit 208 will be described in detail below (refer to FIGS. 9 to 11). Setting of the operation mode may be performed by assigning an operation mode setting function to the function button BT3 (refer to FIG. 1) of the hand operation part 102 as described above.

<Configuration of Storage Unit>

Figures 5, 6:
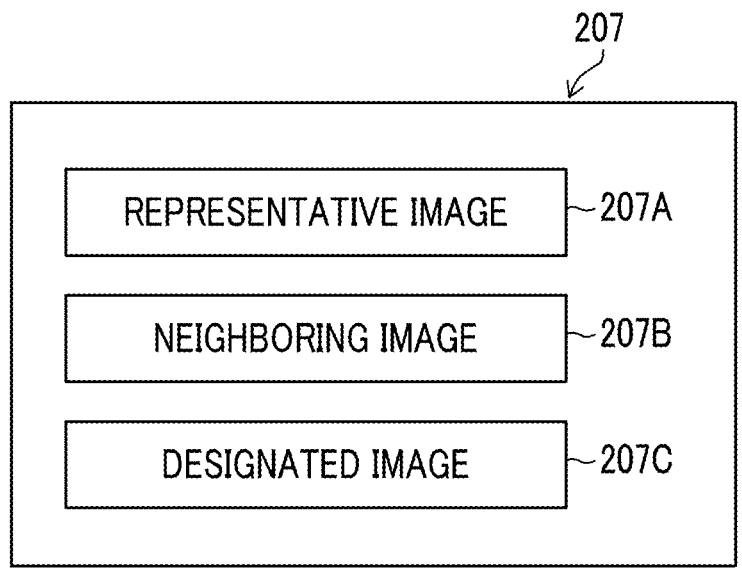
FIG. 5 is a diagram showing information stored in a storage unit.
FIG. 6 is a diagram showing an aspect of association between a representative image and neighboring images.

The storage unit 207 (representative image storage unit, neighboring image storage unit, designated image preservation unit, recording device) is formed by a non-temporary recording medium such as a compact disk (CD), a digital versatile disk (DVD), a hard disk, and various semiconductor memories, and stores information and images shown in FIG. 5 in association with each other. As shown in FIG. 5, the storage unit 207 stores a representative image 207A, a neighboring image 207B (including the diagnosis neighboring image), and a designated image 207C. The representative image 207A (representative image) and the neighboring image 207B (neighboring image) are recorded being associated with each other as shown in FIG. 6, for example. In FIG. 6, "i101" and the like are identification information of images. The designated image 207C (designated image) is an image designated from among the representative image 207A and the neighboring image 207B (refer to FIG. 20). The images are displayed on the monitor 400 by an operation, which is performed through the operation unit 208, and the control of the CPU 210 and/or the image processing unit 204.

The storage unit 207 (recording device) may store analysis results regarding any one or both of a notable region (region of interest), which is a region to be notable, included in the image for medical use (medical image) and the presence or absence of the object to be notable. In this case, the image processing unit 204 (medical image analysis processing unit, medical image analysis result acquisition unit) can display the analysis results on the monitor 400 by acquiring the analysis results from the storage unit 207.

<Configuration of Display Device>

Figure 10:
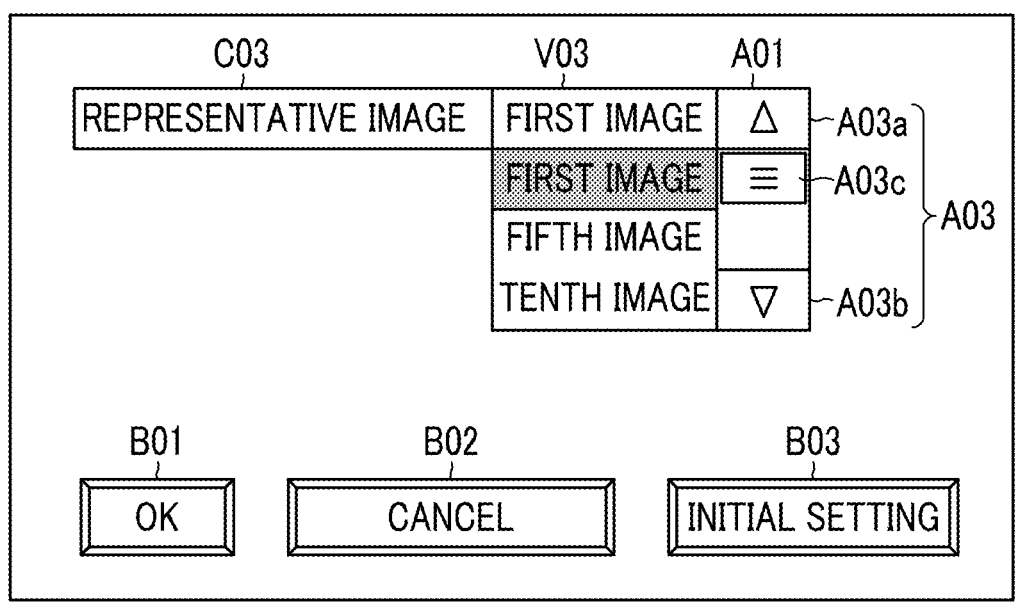
FIG. 10 is a diagram showing another example of the imaging condition setting screen.
Figure 11:
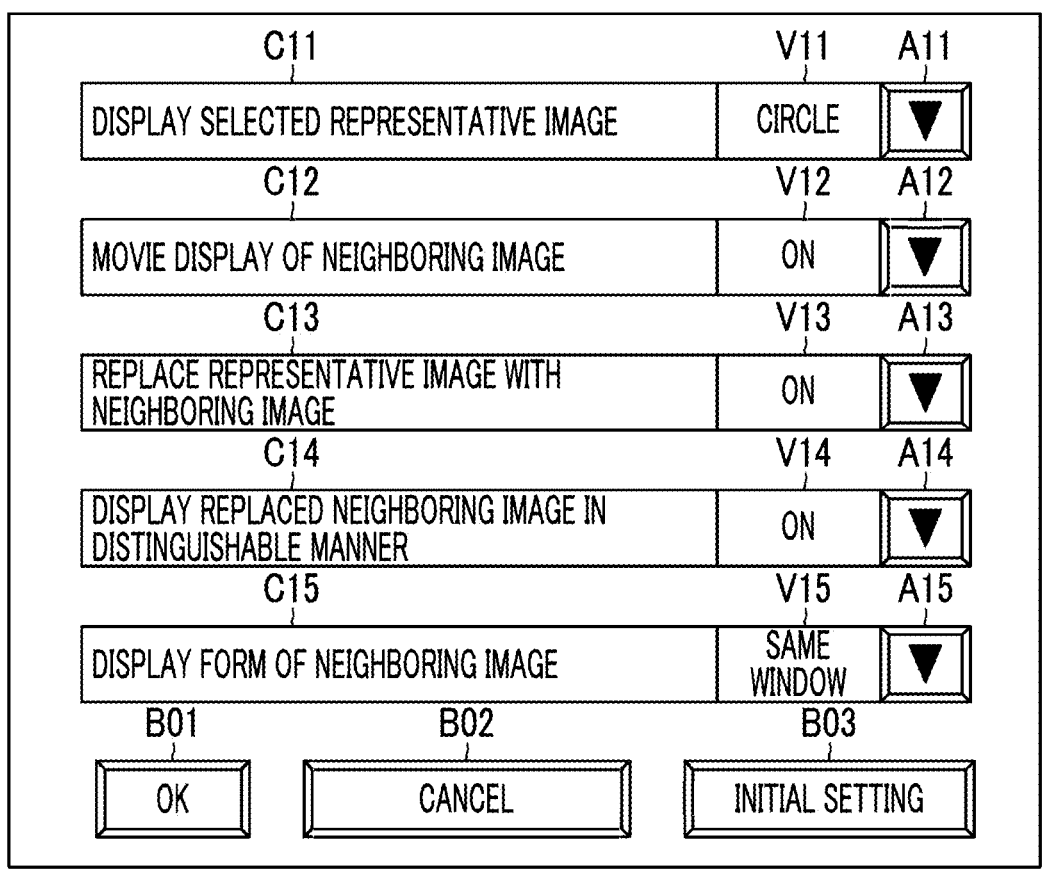
FIG. 11 is a diagram showing an example of a display condition setting screen.

The monitor 400 (display device) displays the representative image, the neighboring image, the imaging condition setting screen, the display condition setting screen, and the like by the operation, which is performed through the operation unit 208, and the control of the CPU 210 and/or the image processing unit 204 (refer to FIGS. 9 to 11). Further, the monitor 400 includes a touch panel that is used to perform an operation for setting an imaging condition and/or an operation for setting a display condition.

<Processing of Diagnosis Support Method>

Figure 7:
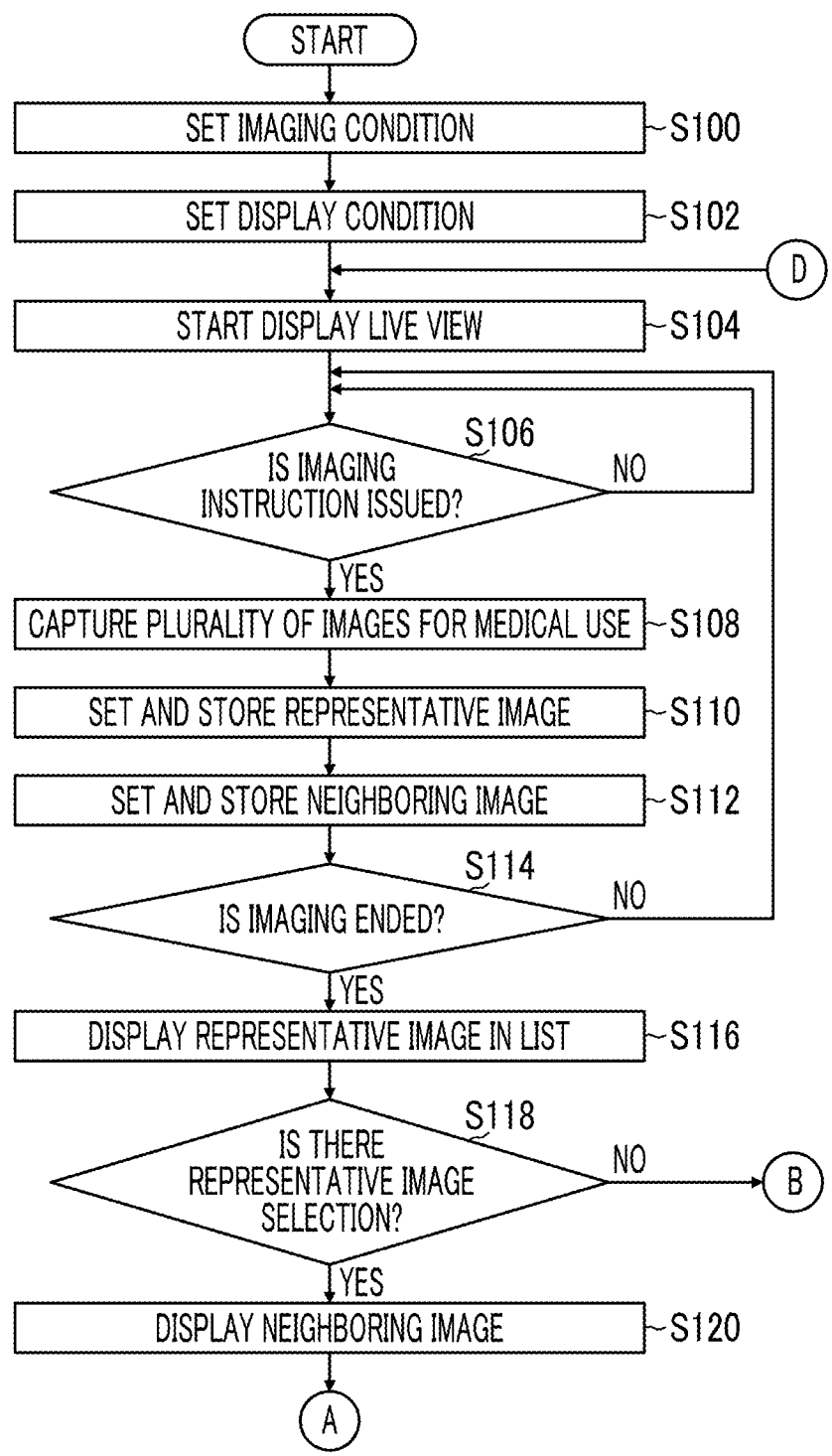
FIG. 7 is a flowchart showing processing of a diagnosis support method.

A diagnosis support method for an object to be examined, using the endoscope system 10 will be described. FIGS. 7 and 8 are flowcharts showing a procedure of the diagnosis support method according to the first embodiment.

<Setting of Imaging Condition>

In the flowcharts of FIGS. 7 and 8, setting of the imaging condition and the display condition is performed on the basis of the user's instruction prior to the imaging (steps S100 and S102). However, the setting may be performed during the imaging or after the imaging. FIG. 9 is a diagram showing an example of an imaging condition setting screen. In FIG. 9, regarding each item of the imaging conditions, a condition name (regions C01 to C10), the contents of the setting condition (regions V01 to V10), and a pull-down button (buttons A01 to A10) are shown. A button B01 is a button for confirming the display conditions, a button B02 is a button for cancelling the condition change, a button B03 is a button for returning the conditions to initial setting, and the buttons B01 to B03 are provided in a lower portion of the screen. The screen in FIG. 9 is displayed on the monitor 400, and the display condition can be set by the user's operation via the touch panel of the monitor 400 and/or the keyboard and mouse (not shown) of the operation unit 208.

The regions C01 and V01 indicate the number of images to be acquired through single-shot imaging, and the number of images to be acquired can be designated by a selection operation through the button A01. The regions C02 and V02 indicate an imaging period, and the imaging period can be designated by an operation through the button A02. Images of which the number is designated by the region C01 or the like can be acquired in the imaging period designated by the region C02 or the like. The regions C03 and V03 indicate "what numberth image among the images acquired through single-shot imaging is set as a representative image", and a specific numerical value (first, fifth, tenth, and the like) can be selected by an operation through the button A03.

FIG. 10 is a diagram showing an example of a screen for setting the number of the representative image, in a case where the button A03 is designated in the screen of FIG. 9 by an operation of the touch panel of the monitor 400, or an operation or the like through the operation unit 208 (the same is applied for other items), the region V03 becomes a pull-down display state to transition to the state in FIG. 10. Illustration of items other than the number of the representative image is omitted in FIG. 10. In FIG. 10, numerical values settable as the number of the representative image are displayed in the region V03 (1 to 10 in this case, but only some values can be settable), and, for setting a value, a user may select a numerical value by moving a selection range up and down using buttons A03a and A03b and a slide bar A03c, and designate the button B01 (OK button). In a case where the button B01 is designated in the state of FIG. 10, "the first image" becomes the representative image.

The regions C04 and V04 of FIG. 9 indicate "whether to automatically detect a region of interest from the captured image", and ON (automatically detecting) or OFF (not automatically detecting) can be selected by a selection operation through the button A04. In a case where ON is selected, a region of interest (lesion region, lesion candidate region, and the like; referred to as notable region) is detected by the image processing unit 204 (region-of-interest detection unit 204I). The regions C05 and V05 indicate "whether to automatically perform imaging in a case where a region of interest has been detected", and ON (automatically imaging) or OFF (not automatically imaging) can be selected by a selection operation through the button A05. In a case where ON is selected, according to the detection of the region of interest by the region-of-interest detection unit 204I, the image processing unit 204 (imaging control unit 204C) controls the imaging optical system 130 to perform imaging.

The regions C06 and V06 indicate "whether to automatically detect an instrument or the like from the captured image", and ON (automatically detecting) or OFF (not automatically detecting) can be selected by a selection operation through the button A06. The "instrument or the like" includes a treatment tool (for example, forceps, needle, clip, tube, and the like) for performing biopsies, excision, and the like on an object to be examined, and can be inserted into the object to be examined through the forceps port 126. The regions C07 and V07 indicate "whether to automatically perform imaging in a case where an instrument or the like has been detected", and ON (automatically imaging) or OFF (not automatically imaging) can be selected by a selection operation through the button A07. In a case where ON is selected, according to the detection of the instrument or the like by the image analysis unit 204K, the image processing unit 204 (imaging control unit 204C) controls the imaging optical system 130 to perform imaging.

Similar to the regions C06 and V06, the regions C08 and V08 indicate "whether to automatically detect a pigment or the like from the captured image", and ON (automatically detecting) or OFF (not automatically detecting) can be selected by a selection operation through the button A08. The "pigment or the like" means an agent including a pigment and a dye for observing the shape, unevenness, and the like of a lesion. Further, the regions C09 and V09 indicate "whether to automatically perform imaging in a case where a pigment or the like has been detected", and ON (automatically imaging) or OFF (not automatically imaging) can be selected by a selection operation through the button A09. In a case where ON is selected, according to the detection of the pigment or the like by the image analysis unit 204K, the image processing unit 204 (imaging control unit 204C) controls the imaging optical system 130 to perform imaging.

The regions C10 and V10 indicate "whether to automatically extract a diagnosis neighboring image", and ON (automatically detecting) or OFF (not automatically detecting) can be selected by a selection operation through the button A10. The "diagnosis neighboring image" means an image suitable for the diagnosis among the neighboring images, and is extracted on the basis of at least one of exposure, shaking, presence of a region of interest, an instrument or the like and/or use of a pigment or the like. In a case where ON is selected, the diagnosis neighboring image is extracted on the basis of the analysis results of the neighboring images by the image analysis unit 204K. An extraction condition is set by an operation through regions C10a and V10a and a button A10a.

The condition setting in FIGS. 9 and 10 is an example, and addition or deletion of a condition, or a change of the contents (numerical value or the like) of a condition may be performed. For example, a region for setting an imaging timing (imaging timing determined by ON or OFF of interval imaging in which imaging is performed at a certain interval, and an imaging interval in case of performing the interval imaging) on the basis of an input of a user's instruction can be provided. In this case, the imaging timing setting unit 204A (imaging timing setting unit) sets an imaging timing on the basis of the set condition, and according to the set imaging timing, the imaging control unit 204C (imaging control unit) issues an imaging instruction to the imaging optical system 130 (image-for-medical-use capturing unit) to perform imaging.

<Setting of Display Condition>

FIG. 11 is a diagram showing an example of a display condition setting screen of the representative image and the neighboring image. Regions C11 and V11 indicate an aspect of displaying the selected representative image in a distinguishable manner, and marking with a circle, addition of a frame border, graying out of images other than the selected image, and the like can be designated by a selection operation through a button A11 (refer to FIGS. 14A to 18). Regions C12 and V12 indicate "whether to perform movie display of the neighboring images which are associated with the selected representative image" (refer to FIGS. 17A to 17C), and ON or OFF can be designated by a selection operation through a button A12. Regions C13 and V13 indicate "in case of selecting any one of the neighboring images, whether to replace the representative image with the selected neighboring image", and ON or OFF can be designated by a selection operation through a button A13. Regions C14 and V14 indicate "in case of replacing the representative image with the neighboring image, whether to display the replaced neighboring image in a distinguishable manner" (refer to FIG. 14C), and ON or OFF can be designated by a selection operation through a button A14. Regions C15 and V15 indicate a display form of the neighboring image in case of selecting the representative image, and the "same window (the same window as the representative image)" (refer to FIG. 14B), a "different window" and the like (refer to FIGS. 16A to 17C) can be designated by a selection operation through a button A15.

In a case where setting of the imaging condition and the display condition in steps S100 and S102 is ended and the insertion part 104 of the endoscope body 100 is inserted into an object to be examined, acquisition of live view images by the imaging optical system 130 and the image processing unit 204 (imaging control unit 204C) and display on the monitor 400 are started (step S104). In this manner, a user can observe an aspect inside an object to be examined. In a case where the user performs an insertion operation and a bending operation of the insertion part 104 to direct the hard distal end portion 116 toward a desired direction, and operates the imaging button BT4, the imaging instruction receiving unit 204B (imaging instruction receiving unit) receives an imaging instruction operation. In this manner, the determination (presence or absence of imaging instruction) in step S106 is affirmative and the processing proceeds to step S108 (imaging control step), and a plurality of images for medical use (medical images) are acquired by the imaging optical system 130 (image-for-medical-use capturing unit, imaging device, medical image acquisition unit) and the imaging control unit 204C (imaging control unit, medical image acquisition unit). Further, even in a case where there is no operation of the imaging button BT4, in a case where automatic imaging (refer to FIG. 9) according to the detection of the region of interest, the detection of the pigment, and the like is ON, if the setting conditions are satisfied, an imaging instruction is issued by the imaging control unit 204C (YES in step S106) and a plurality of images for medical use are captured (step S108).

In a case where a plurality of images for medical use are acquired in step S108, any one of the acquired images for medical use is set as a representative image (representative image 207A) in an imaging period by the representative image storage unit 204D (representative image storage unit), and is stored in the storage unit 207 (step S110: representative image storage step). Further, images other than the representative image among the acquired images for medical use are set as neighboring images (neighboring images 207B) by the neighboring image storage unit 204E (neighboring image storage unit), and are stored in the storage unit 207 being associated with the representative image (step S112: neighboring image storage step).

<Storage of Representative Image and Neighboring Image>

Figure 12A:
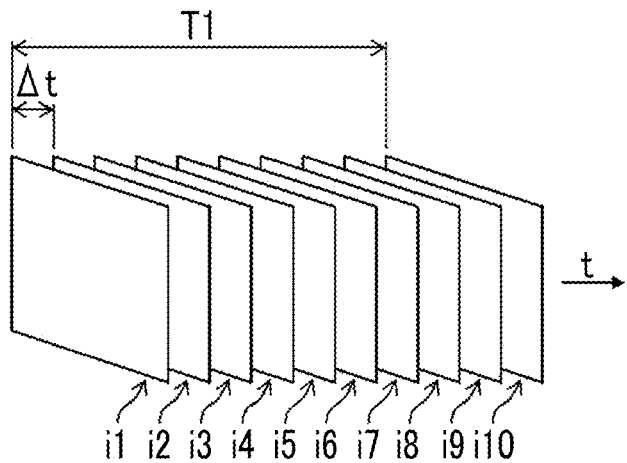
FIGS. 12A to 12D are diagrams showing examples of storing the representative image and the neighboring images.
Figure 12B:
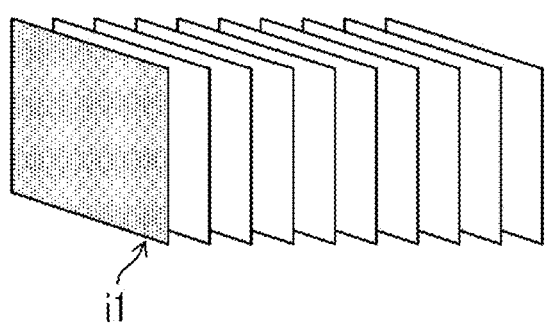
Figure 12C:
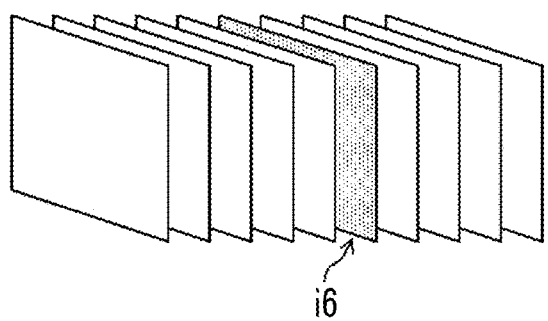
Figure 12D:
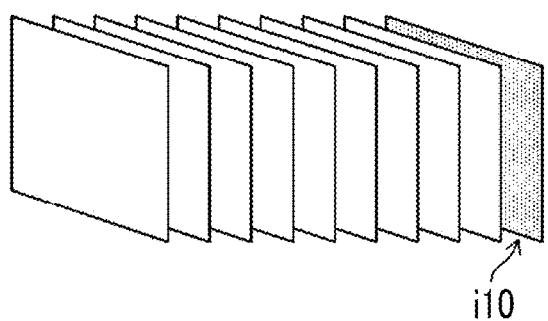

FIGS. 12A to 12D are diagrams showing examples of storing the representative image and the neighboring images. Here, it is assumed that 10 images (images i1 to i10) are acquired (imaging interval: Δt) in an imaging period T1 as shown in FIG. 12A. In this case, the image i1 which is captured first in the imaging period T1 may be set as the representative image and the remaining images (images i2 to i10) may be set as the neighboring images as shown in FIG. 12B, or the image i6 which is captured in the middle of the imaging period T1 may be set as the representative image and the remaining images (images i1 to i5 and images i7 to i10) may be set as the neighboring images as shown in FIG. 12C. Further, the image i10 which is captured last in the imaging period T1 may be set as the representative image and the remaining images (images i1 to i9) may be set as the neighboring images as shown in FIG. 12D. Which image is set as the representative image can be set in the imaging condition setting screen as shown in FIG. 9 as described above (step S100).

<Storage of Representative Image and Neighboring Image (Other Examples)>

Figure 13:
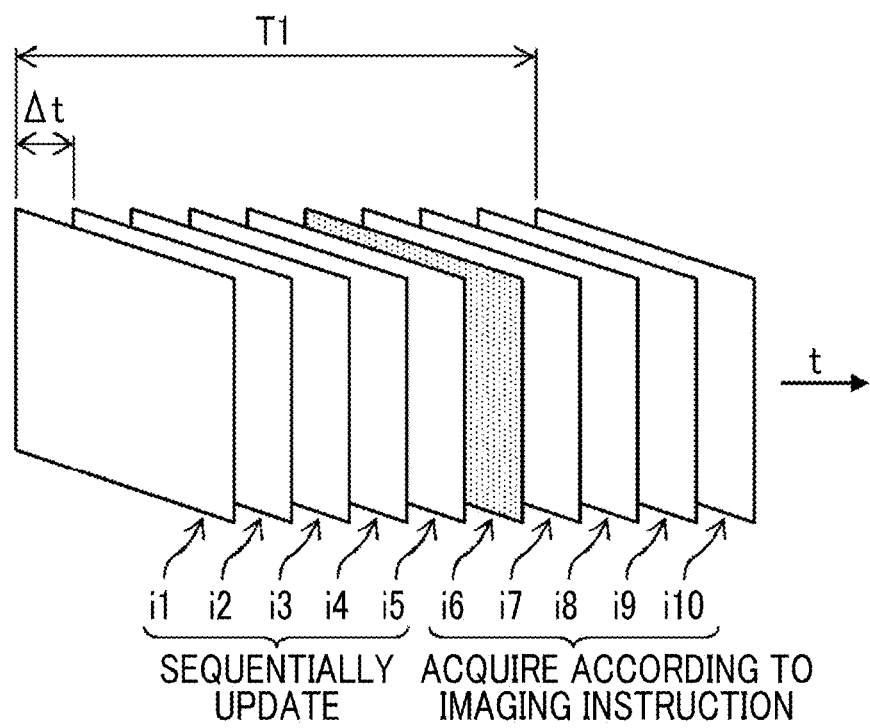
FIG. 13 is a diagram showing another example of storing the representative image and the neighboring images.

FIG. 13 is a diagram showing another example of storing the representative image and the neighboring images. In the examples shown in FIGS. 12A to 12D, a plurality of images for medical use are acquired according to the imaging instruction. However, in the example in FIG. 13, regardless of the presence or absence of the imaging instruction, acquisition of the images by the imaging control unit and the imaging optical system 130 is continued, and a certain number (here, 5) of images are temporarily stored in the buffer (RAM 212) and are sequentially updated (the oldest image is deleted whenever one image is acquired). The images acquired in this manner are images i1 to i5. In a case where an imaging instruction by the user is issued (YES in step S106), a plurality of images for medical use are further acquired according to the imaging instruction (step S108). In the example of FIG. 13, the images for medical use acquired according to the imaging instruction are five (images i6 to i10). In the example of FIG. 13, any one of the images i1 to i5 recorded in the buffer or the images i6 to i10 acquired according to the imaging instruction is set as the representative image (representative image 207A) and is stored in the storage unit 207 (step S110: representative image storage step), and the remaining images are set as the neighboring images (neighboring images 207B) and are stored being associated with the representative image (step S112: neighboring image storage step). The image i6 is set as the representative image in FIG. 13, but another image (image i1, i10, or the like) may be set as the representative image.

Acquisition of a plurality of images for medical use, and storage of the representative images and the neighboring images as shown in FIGS. 12A to 13 are continued until imaging is ended (YES in step S114).

<Display and Selection of Representative Image, and Display of Neighboring Image (Aspect 1)>

Figure 14A:
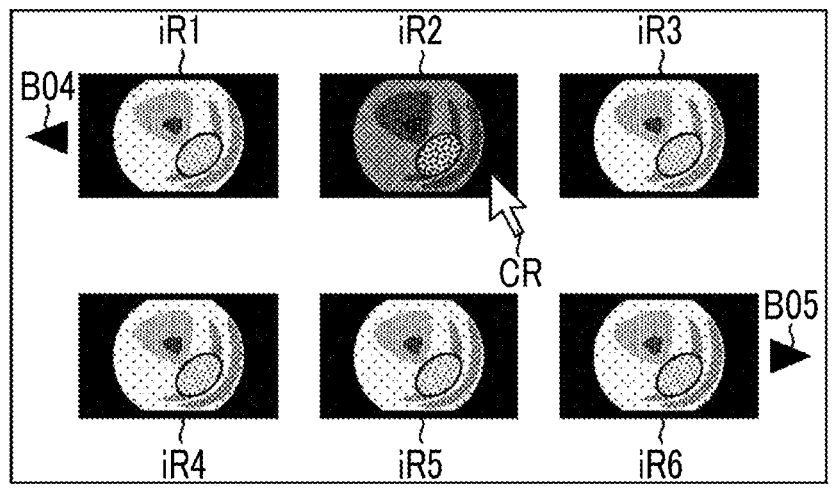
FIGS. 14A to 14C are diagrams showing display examples of the representative images and the neighboring images.

In a case where acquisition of a plurality of images for medical use and storage of the representative images and the neighboring images are ended, the representative images are displayed in a list on the monitor 400 by the representative image display control unit 204F (representative image display control unit) (step S116: representative image display control step). FIG. 14A is a diagram showing a display example of the representative images. Here, representative images iR1 to iR6 are displayed. A button B04 is a button for causing images which are captured before the displayed images to be displayed, and a button B05 is a button for causing images which are captured after the displayed images to be displayed.

Figure 14B:
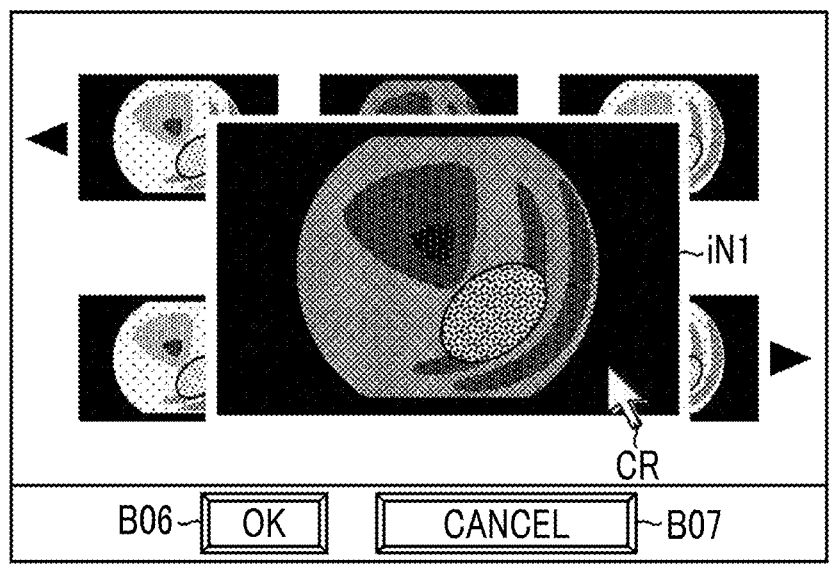

Among the representative images iR1 to iR6 shown in FIG. 14A, it is assumed that the representative image iR2 is not suitable for diagnosis because of poor exposure. Thus, in a case where the user operates a cursor CR by using the mouse of the operation unit 208 to select the representative image iR2 (YES in step S118 (representative image selection step)), the neighboring image which is associated with the representative image iR2 is displayed in an enlarged manner to overlap the representative images iR1 to iR6 as shown in FIG. 14B (step S120: neighboring image display control step). Here, an aspect in which a neighboring image iN1 is displayed is shown. As shown in Aspect 1 and other aspects described below, the neighboring image display control unit 204H changes at least one of a display position, a display window, or a display size of the neighboring image to be different from the representative image.

In a case where the user operates the operation unit 208, a switching instruction of the neighboring image is received (YES in step S122), the displayed neighboring image iN1 is switched to another neighboring image of which the imaging time is different from that of the neighboring image iN1 (step S124: neighboring image display control step). By such an operation (switching instruction), the user can select an image suitable for diagnosis from among the neighboring images. Examples of an operation of switching the neighboring images include an operation of arrow keys (up/down or right/left) of the keyboard, clicking of the mouse button, rolling of the scroll wheel, an operation of a foot pedal (not shown), and the like, but the operation is not limited thereto.

In a state where a certain representative image (for example, representative image iR2) is selected and neighboring images are displayed, in a case where another representative image (for example, representative image iR4) is selected, the display of the neighboring images which are associated with the previously selected representative image (representative image iR2 in this case) is ended. Further, the display form of the representative image iR2 is returned to a state where the representative image iR2 is not selected (display in a distinguishable manner, such as marking with a circle or the like is ended). Together with this, the newly selected representative image (representative image iR4 in this case) is displayed in a distinguishable manner and neighboring images which are associated with the representative image are displayed.

The above-described processing is performed, under the control of the CPU 210, by the image processing unit 204 (specifically, representative image display control unit 204F (representative image display control unit), the representative image selection unit 204G (representative image selection unit), the neighboring image display control unit 204H (neighboring image display control unit), the switching instruction receiving unit 204J (switching instruction receiving unit)).

Figure 14C:
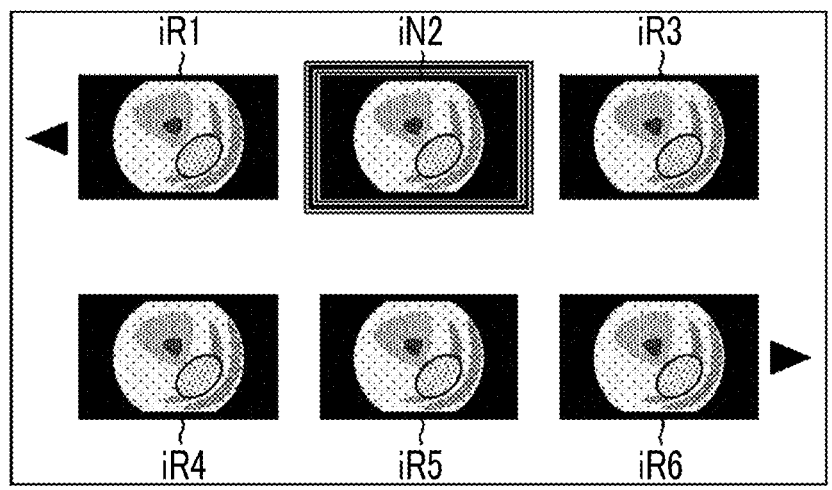

In a case where the user performs the above-described operation to select a desired neighboring image and operates a button B06 by using the mouse, selection of the neighboring image is confirmed (YES in step S126; NO until the selection is confirmed). In a case where a button B07 is operated, the display of the neighboring images which are associated with the representative image (representative image iR2 in the examples of FIGS. 14A to 14C) is ended, and the display is returned to a list display state of the representative images (refer to FIG. 14A). In this case, in a case where "replacing of the representative image with the neighboring image" as described in the regions C13 and V13 of FIG. 11 is ON, the selected neighboring image is displayed instead of the originally displayed representative image iR2 as shown in FIG. 14C (step S128). Here, an aspect in which a neighboring image iN2 is displayed is shown.

In this manner, in the endoscope system 10 according to the first embodiment, regarding a representative image selected from representative images which are displayed in a list, any one of a medical image in a group of neighboring images which are associated with the selected representative image is displayed on the display device (monitor 400), and thereby an image suitable for diagnosis can be easily displayed. Further, since the representative image and the neighboring images are captured within the imaging period, an image change between the representative image and the neighboring images (change in position or direction of a subject, exposure conditions, and the like in images) can be reduced. The length of the imaging period can be set in the imaging condition setting screen (refer to FIG. 9) such that the change between the representative image and the neighboring images is in an allowable range.

As described in setting of the display condition, in a case where setting of "displaying the replaced neighboring image in a distinguishable manner" is ON (refer to the regions C14 and V14 of FIG. 11), when the representative image is switched to the neighboring image, the replaced neighboring image is displayed in a distinguishable manner (a frame border is added to the neighboring image iN2 in the example of FIG. 14C). By such display in a distinguishable manner, it is possible to easily grasp which image is switched/replaced.

<Another Aspect (Aspect 2) of Display and Selection of Image>

Figure 15A:
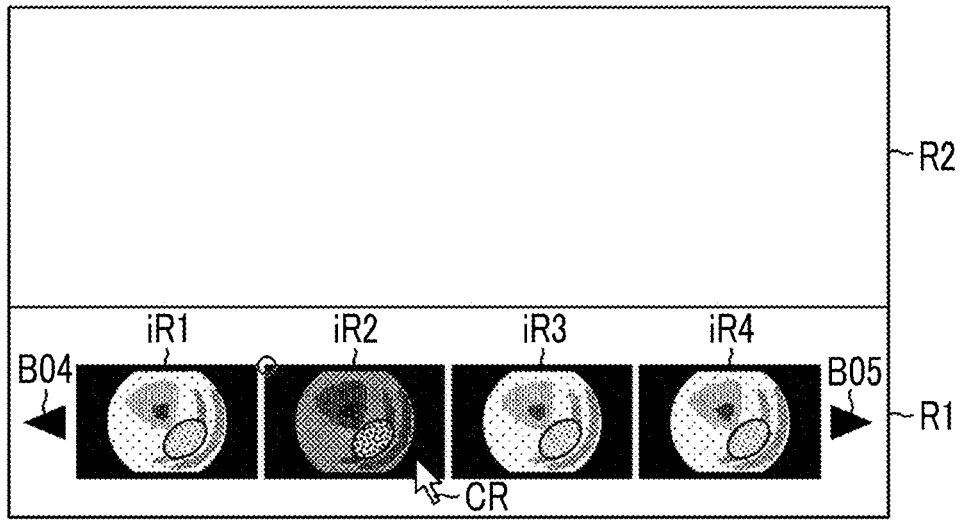
FIGS. 15A to 15C are diagrams showing other display examples of the representative image and the neighboring image.
Figure 15B:
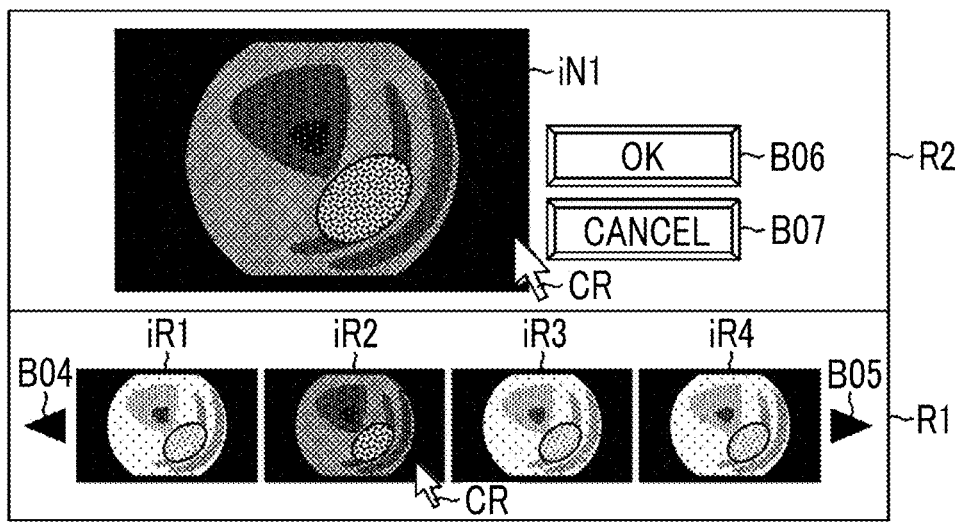
Figure 15C:
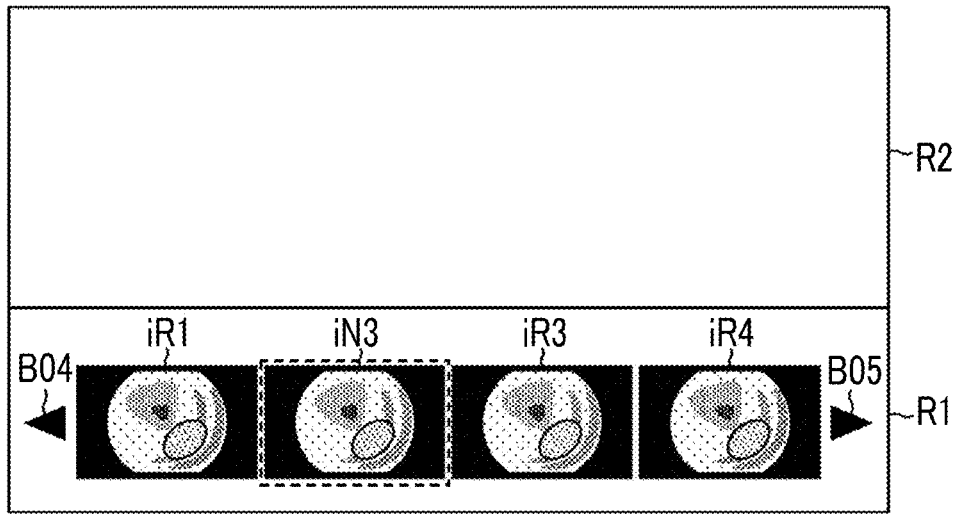

Another aspect (Aspect 2) of the display and selection of the representative image and the neighboring image will be described. FIGS. 15A to 15C are diagrams showing an aspect in which the representative image and the neighboring image are displayed in different regions on the same window. In the examples of FIGS. 15A to 15C, as shown in FIG. 15A, representative images (representative images iR1 to iR4) are displayed in a list in a display region R1 of the monitor 400 (step S116). In a case where a representative image (here, representative image iR2) is selected (YES in step S118), any one of neighboring images (here, neighboring image iN1) which are associated with the selected representative image is displayed in an enlarged manner in a display region R2 which is a different region from the display region R1 on the same window (step S120: refer to FIG. 15B). A switching operation for the displayed neighboring image is the same as that shown in FIGS. 14A to 14C (steps S122 to S126). That is, in a case where the button B06 is operated, the neighboring image is confirmed (YES in step S126), and the selected neighboring image (here, neighboring image iN3) is displayed in the display region R1 instead of the originally displayed representative image iR2 as shown in FIG. 15C (step S128). In this case, according to the setting of the display condition setting screen (refer to FIG. 11), the neighboring image iN3 which is displayed instead of the representative image iR2 is displayed in a distinguishable manner (here, addition of a frame border) in the same manner as shown in FIG. 14C.

<Still Another Aspect (Aspect 3) of Display and Selection of Image>

Figure 16A:
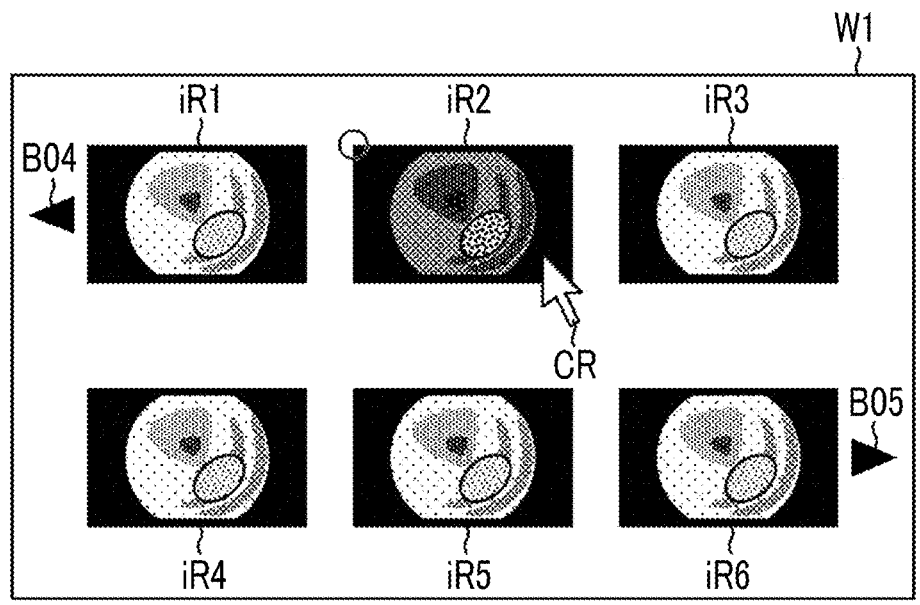
FIGS. 16A and 16B are diagrams showing still other display examples of the representative images and the neighboring images.
Figure 16B:
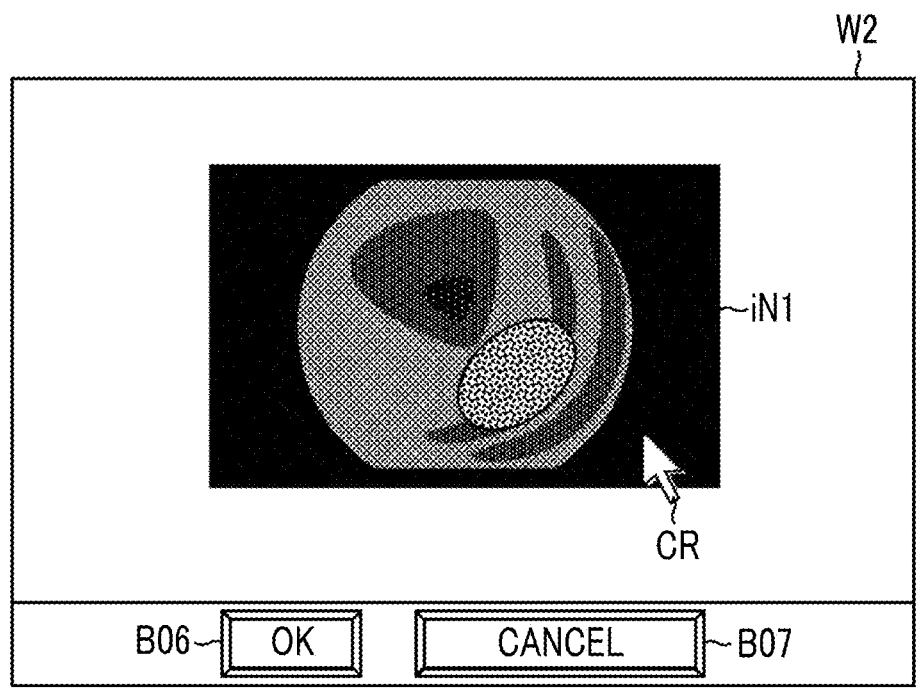

Still another aspect (Aspect 3) of the display and selection of the representative image and the neighboring image will be described. FIGS. 16A and 16B are diagrams showing an aspect in which the representative image and the neighboring image are displayed in different windows. In the examples of FIGS. 16A and 16B, as shown in FIG. 16A, representative images (representative images iR1 to iR6) are displayed in a list on a window W1 of the monitor 400, by the representative image display control unit 204F (step S116). In a case where a representative image (here, representative image iR2) is selected (step S118), any one of neighboring images (here, neighboring image iN1) which are associated with the selected representative image is displayed in an enlarged manner on a window W2 which is different from the window W1 (step S120: refer to FIG. 16B). A switching operation for the displayed neighboring image is the same as that shown in FIGS. 14A to 14C and in FIGS. 15A to 15C (steps S122 to S126). That is, in a case where the button B06 is operated, the neighboring image is confirmed (YES in step S126), and the selected neighboring image (here, neighboring image iN3) is displayed on the window W1 instead of the originally displayed representative image iR2 in the same manner as in FIG. 14C (step S128).

<Still Another Aspect (Aspect 4) of Display and Selection of Image>

Figure 17A:
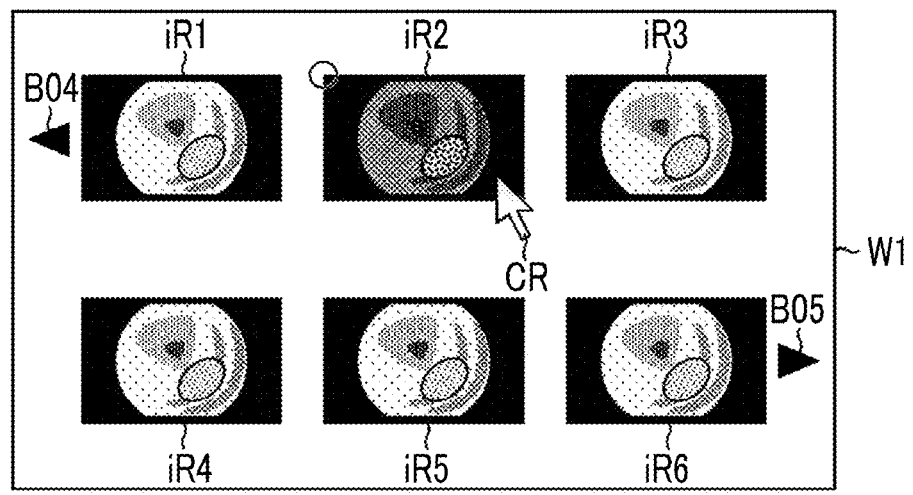
FIGS. 17A to 17C are diagrams showing aspects of movie display of the neighboring images.
Figure 17B:
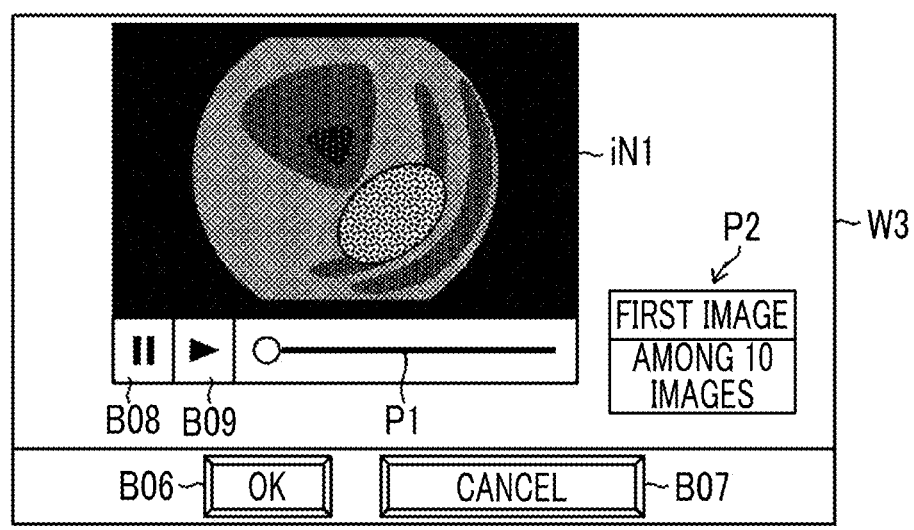
Figure 17C:
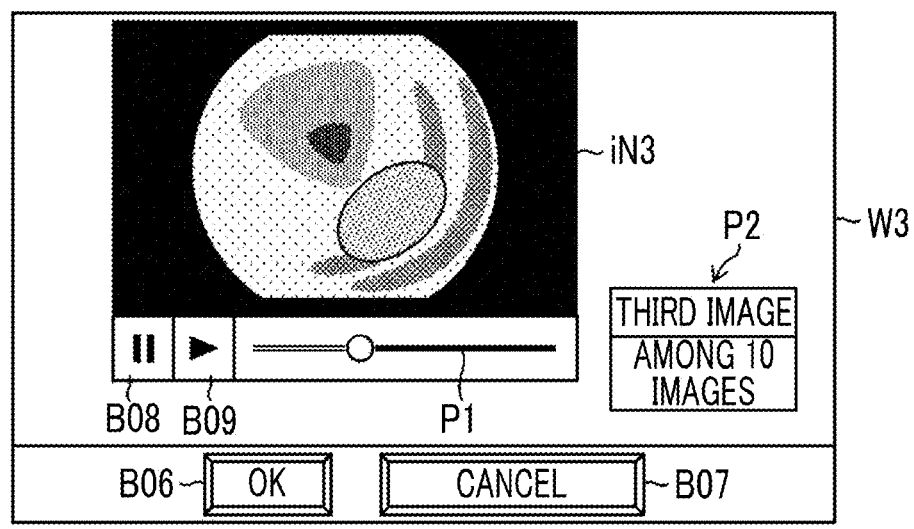

Still another aspect (Aspect 4) of the display and selection of the representative image and the neighboring image will be described. In Aspects 1 to 3, the neighboring image is switched and displayed by the switching operation of the user. However, in Aspect 4, switching display is performed on the basis of the movie display (continuous display, sequential display) of the neighboring images. FIG. 17A shows a state where representative images (representative images iR1 to iR6) are displayed in a list on the window W1 (step S116), and is the same as FIG. 14A and FIG. 16A. In the examples of FIGS. 17A to 17C, in a case where a representative image (here, representative image iR2) is selected (YES in step S118), movie display (continuous display, sequential display) of the neighboring images is started on the window W3 (FIG. 17B; step S119-1 in FIG. 18). FIG. 17B shows a state where a neighboring image iN1 with poor exposure is displayed in the movie display, and FIG. 17C shows a state where a neighboring image iN3 with proper exposure is displayed. In FIGS. 17B and 17C, a button B08 is a button for a display stopping instruction of the movie display, and a button B09 is a button for starting the movie display. Further, an indicator P1 shows a progress status of the movie display, and an indicator P2 shows "what numberth image among how many images the displayed neighboring image is" in conjunction with the indicator P1.

In a case where the user views the movie display and operates the button B08 at a time point at which a suitable neighboring image is displayed, a display stopping instruction of the movie display (continuous display) is issued (YES in step S119-2 in FIG. 18), and the movie display is stopped (step S119-3 in FIG. 18). The neighboring image which is being displayed when the display stopping instruction is received is continuously displayed on the monitor 400 (step S119-4 in FIG. 18). In this state, in a case where the button B06 is operated (YES in step S119-5 in FIG. 18), the selection of the neighboring image is confirmed (step S119-6 in FIG. 18), and the selected neighboring image is displayed on the monitor 400 instead of the originally displayed representative image (step S128).

For example, in a case where the user operates the button B08 in a state shown in FIG. 17C (YES in step S119-2), the movie display is stopped (step S119-3), and a neighboring image iN3 which is being displayed when the operation (display stopping instruction) of the button B08 is received is continuously displayed on the window W3 of the monitor 400 (step S119-4). In this state, in a case where the button B06 is operated (YES in step S119-5), the selection of the neighboring image iN3 is confirmed (step S119-6), and the neighboring image iN3 is displayed instead of the representative image iR2 in the same manner as in FIG. 14C (step S128). In a case where the button B09 is operated in a state where the neighboring image iN3 is displayed, the movie display is re-started.

In cases of Aspects 2 to 4 described above, an image suitable for diagnosis can be easily displayed in the same manner as Aspect 1.

<Another Aspect of Displaying Selected Representative Image in Distinguishable Manner>

Figure 19A:
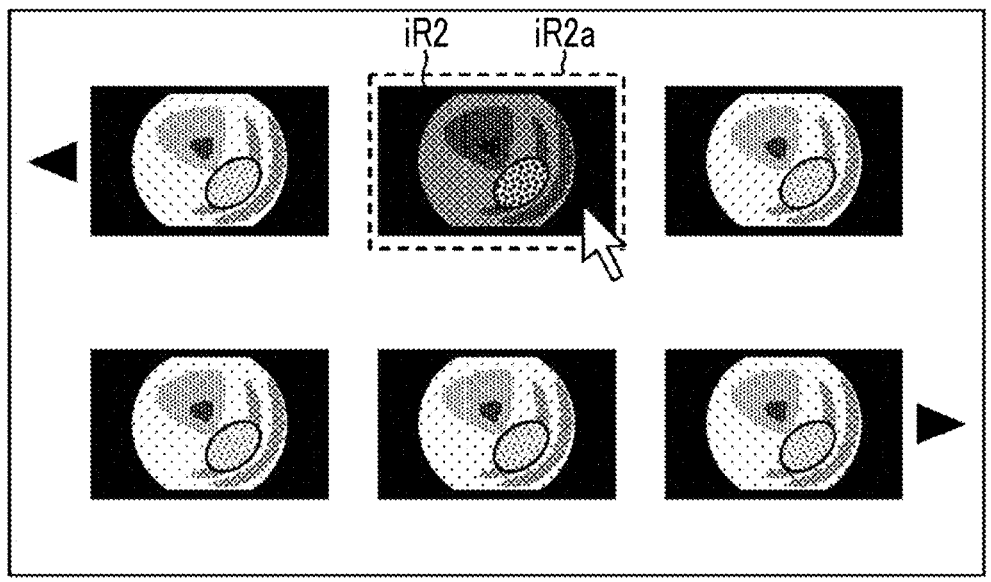
FIGS. 19A and 19B are diagrams showing examples of displaying the selected representative image in a distinguishable manner.
Figure 19B:
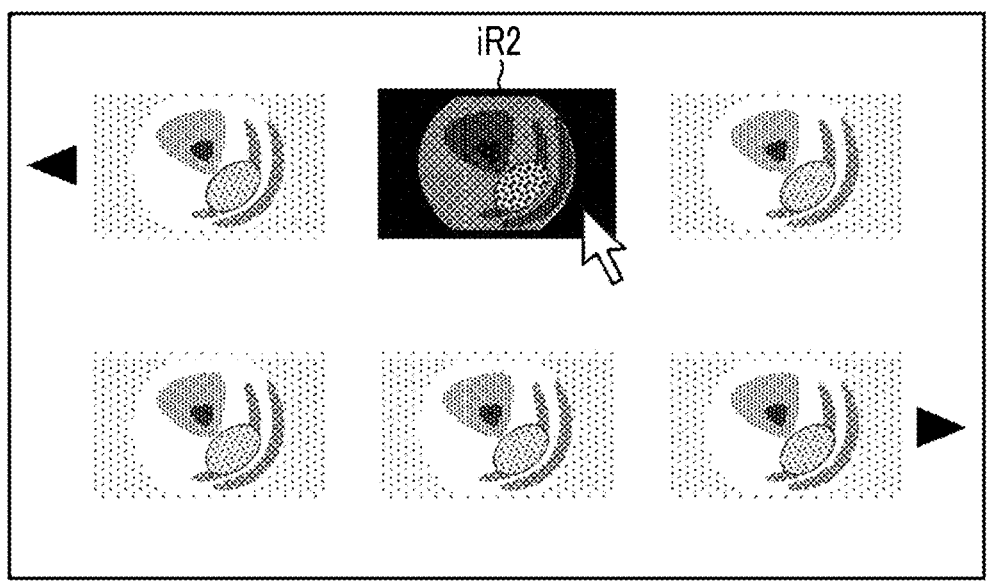

In the examples of FIGS. 14A to 17C, the selected representative image iR2 is marked with a circle, but displaying the selected representative image in a distinguishable manner is not limited to such an aspect. For example, an aspect in which a frame border iR2a is added to the representative image iR2 (selected image) as shown in FIG. 19A, and an aspect in which images other than the representative image iR2 are grayed out (displayed in light gray and excluded from an operation target) as shown in FIG. 19B may be used. The selection of such an aspect can be performed through the display condition setting screen (regions C11 and V11 and button A11) shown in FIG. 11.

<Preservation of Designated Image>

Figure 20:
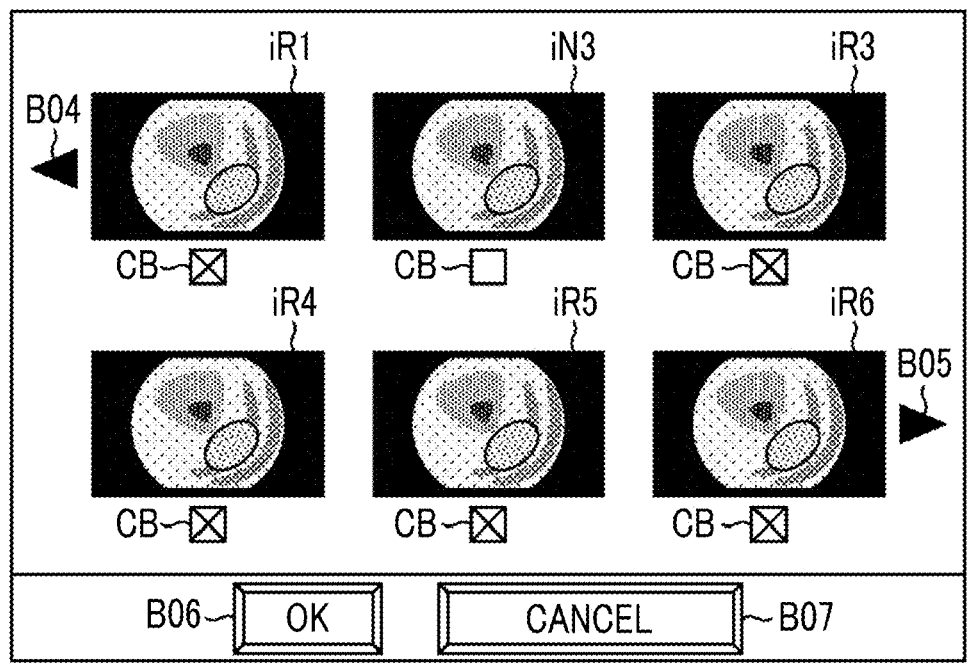
FIG. 20 is a diagram showing an aspect of preservation of a designated image.

In a case where selection and display of the neighboring image which is associated with the representative image are ended by the processing until step S128, the image processing unit 204 (designated image preservation unit 204L) determines whether a preservation image is designated (step S130). This determination can be performed in a manner that a checkbox CB is provided to each image as shown in the example in FIG. 20 and the designated image preservation unit 204L (designated image preservation unit) determines whether there is a checked image at the time point at which the button B06 is operated. Images of which the checkbox is checked (in the example of FIG. 20, representative images iR1, iR3, iR4, iR5, and iR6) are preserved in the storage unit 207 as the designated images 207C (step S132). These images can be attached (associated) to a template of a diagnostic report, and thus report creation can be efficiently performed.

In a case where the designated image is preserved, the CPU 210 and the image processing unit 204 determine whether to end the processing (step S134). In case of YES, the processing is ended, and in case of NO, the processing returns to the display start of the live view image in step S104.

<Another Aspect of Imaging and Display>

Another aspect of the imaging and display of the medical image will be described below. An aspect described below can be executed according to the setting through the imaging condition setting screen (FIGS. 9 and 10) and the display condition setting screen (FIG. 11).

<Automatic Imaging according to Detection of Region of Interest>

Figure 21:
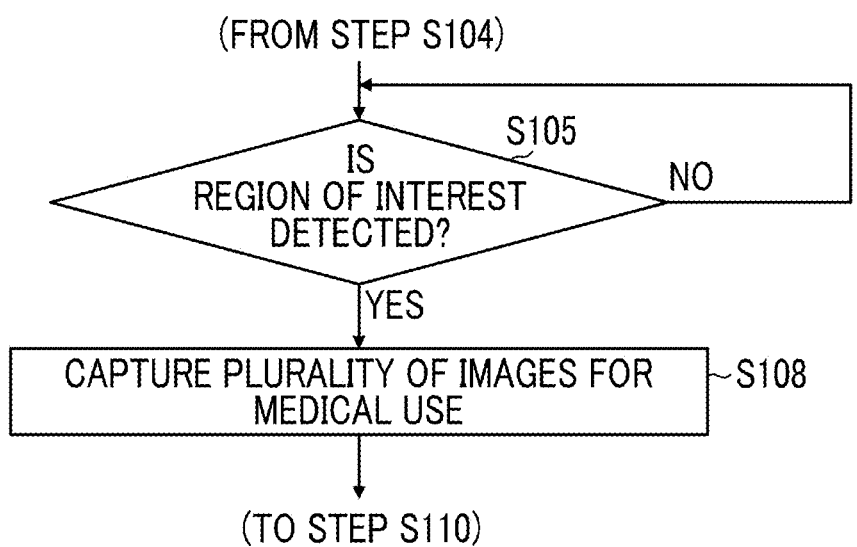
FIG. 21 is a flowchart showing processing of automatic imaging according to detection of a region of interest.
Figure 22A:
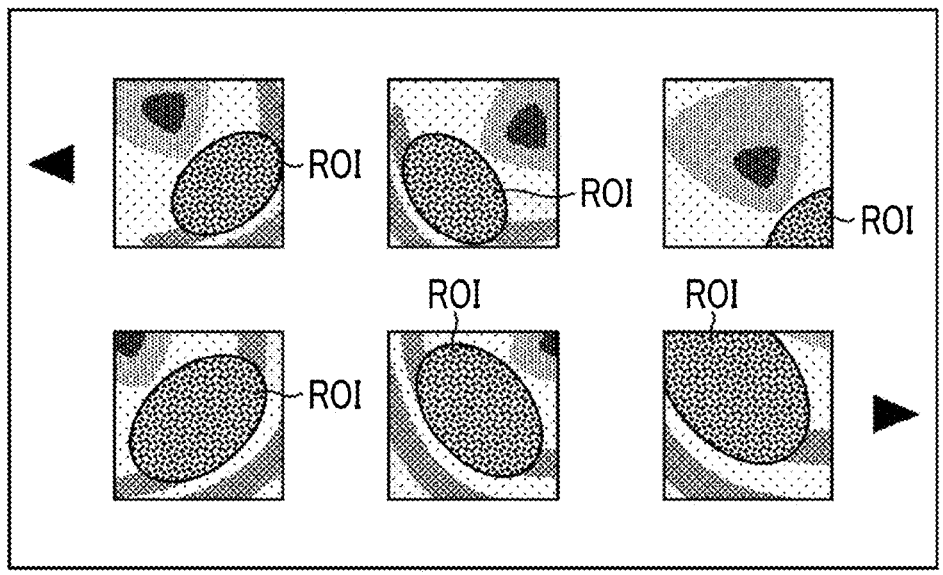
FIGS. 22A and 22B are diagrams respectively showing examples of images captured according to detection of a region of interest and examples of images captured according to detection of an instrument.

In the imaging condition setting screen in FIG. 9, in a case where "detection of a region of interest" (regions C04 and V04) and "automatic imaging" (regions C05 and V05) are ON, the detection of the region of interest and the automatic imaging at the time of detection are executed. Specifically, in a case where the region-of-interest detection unit 204I (region-of-interest detection unit) detects a region of interest in a live view image (YES in step S105 in FIG. 21), a plurality of images for medical use are acquired by the imaging optical system 130 and the imaging control unit 204C (step S108). FIG. 22A shows an aspect in which images (representative images) automatically captured according to the detection of the region of interest ROI are displayed in a list. The extraction of the region of interest (lesion candidate or the like) can be performed by providing, for example, a known computer aided diagnosis (CAD) system to the region-of-interest detection unit 204I. Specifically, it is possible to extract the region of interest (notable region which is a region to be notable) and the presence or absence of a target (target to be notable) in the region of interest on the basis of, for example, a feature quantity of pixels of the medical image. In this case, a result of machine learning (deep learning or the like) in which the images of the region of interest prepared in advance are used as training data may be used.

According to the aspect in which automatic imaging is performed according to the detection of the region of interest, the user can easily display an image suitable for diagnosis, and can efficiently perform report creation. Further, the display of the neighboring images which are associated with the displayed representative image can be performed in the same manner as above described aspects.

Figure 22B:
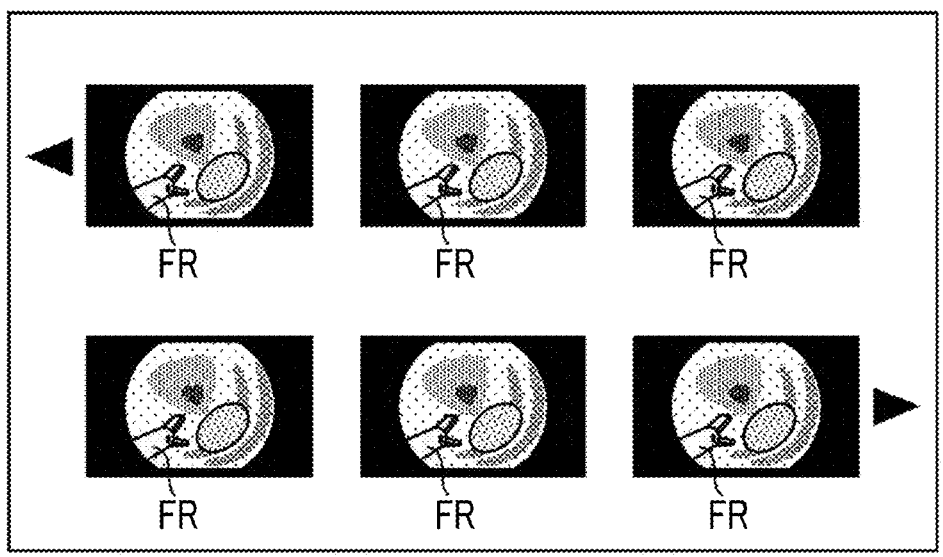

Detection of a pigment, an instrument, or the like and automatic imaging according to the detection can be executed by the condition setting (ON in the regions V06 to V09) through the imaging condition setting screen in FIG. 9, similar to the case of the above-described region of interest. The detection of the pigment can be performed in a manner that, for example, the image analysis unit 204K calculates G/R and B/G as feature quantities from pixel values of red (R), green (G), and blue (B) of the image pick-up element 134 and compares these feature quantities with the feature quantity of each pigment. Further, the detection of an instrument or the like can be performed in a manner that, for example, with an image at the time when each instrument is inserted into the forceps port 126 as a reference image, the image analysis unit 204K compares the reference image with an image at the time of inspection. FIG. 22B shows an aspect in which images (representative images) automatically captured according to the detection of forceps FR are displayed in a list. According to such an aspect, the user can easily display an image suitable for diagnosis, and can efficiently perform report creation. Further, the display of the neighboring images which are associated with the displayed representative image can be performed in the same manner as above described aspects.

<Extraction and Display of Diagnosis Neighboring Image>

Extraction and display of the diagnosis neighboring image can be executed by setting the regions C10 and V10 to ON in the imaging condition setting screen in FIG. 9. The extraction condition can be at least one of presence of a region of interest in the neighboring image, exposure of the neighboring image, a shaking amount of the neighboring image, presence of an instrument in the neighboring image, or use a pigment and/or a dye in the neighboring image. Setting of such a specific extraction condition can be performed by setting a desired condition (one condition or a plurality of conditions may be set) to ON in the same setting screen as in FIG. 10.

Figure 23:
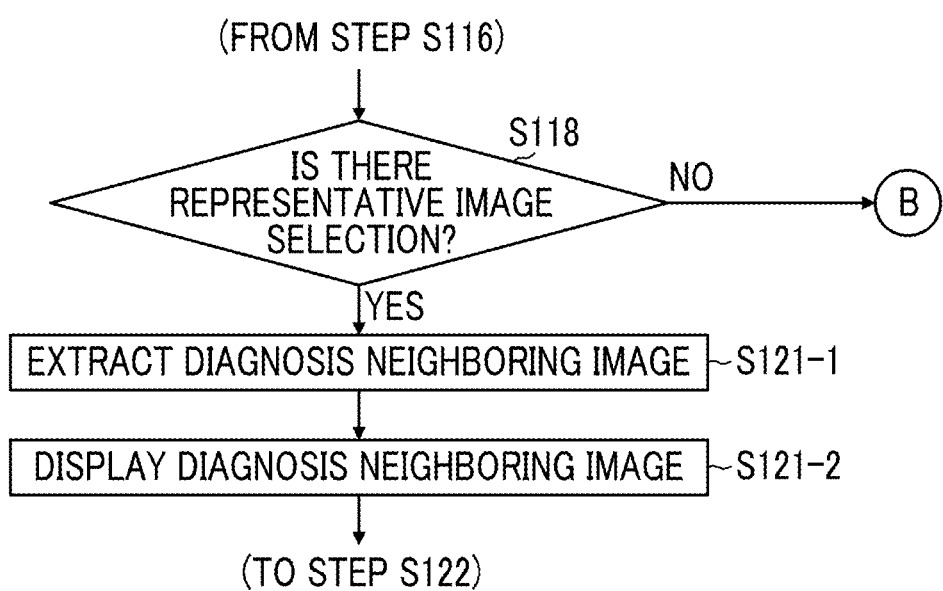
FIG. 23 is a flowchart showing extraction processing of a diagnosis neighboring image.
Figure 24:
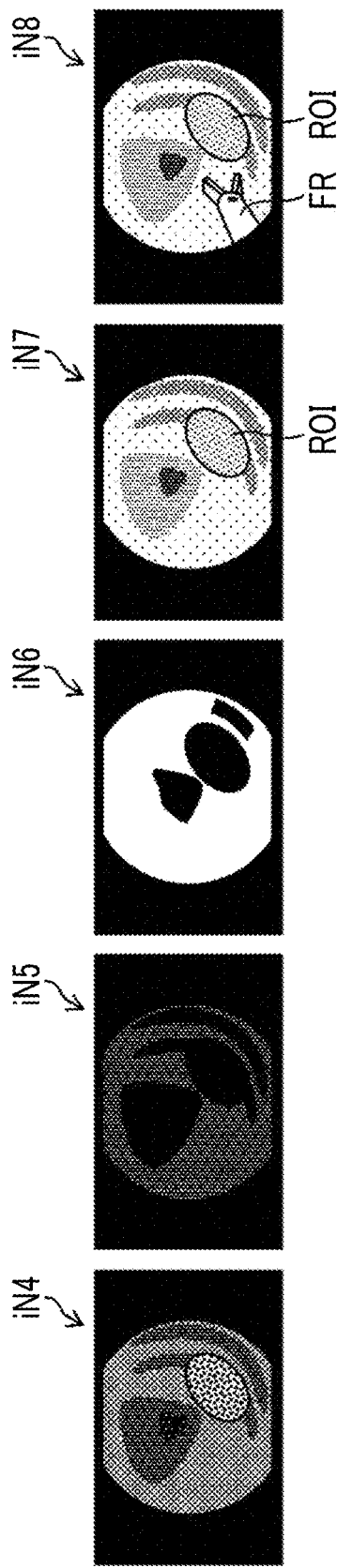
FIG. 24 is a diagram showing an example of extracting the diagnosis neighboring image.

FIG. 23 is a flowchart showing processing of extraction and display of a diagnosis neighboring image. In a case where the regions C10 and V10 is set to ON in the imaging condition setting screen in FIG. 9, if any of representative images displayed in a list (for example, refer to FIG. 14A) is selected (YES in step S118), the image analysis unit 204K extracts a diagnosis neighboring image according to the extraction condition from among a group of neighboring images which is associated with the selected representative image (step S121-1). The extraction condition can be set by an operation through the regions C10a and V10a and the button A10a as described regarding FIG. 9. The neighboring image display control unit 204H displays the extracted diagnosis neighboring image on the monitor 400 (step S121-2). For example, in a case where the neighboring images to be extracted are neighboring images iN4 to iN8 shown in FIG. 24 and the extraction conditions are "proper exposure", "presence of a region of interest", and "presence of an instrument or the like", the neighboring image iN8 in which the exposure is proper and the region of interest ROI and the forceps FR are imaged can be extracted and displayed on the monitor 400. Further, in case of extracting the diagnosis neighboring image, a result of machine learning (deep learning or the like) in which the images for diagnosis prepared in advance are used as training data may be used. By the extraction and display of the diagnosis neighboring image, the user can efficiently perform diagnosis. Further, similar to the preservation of the above-described designated image (refer to FIG. 20), a region-of-interest detection image, a detection image of a pigment and/or an instrument or the like, and a diagnosis neighboring image may be designated, preserved, attached to a template of a report, and the like. In this manner, the user can efficiently perform diagnosis, report creation, and the like.

Additional Remarks

Configuration to be described below is also included in the scope of the invention in addition to the above-described aspects and examples.

Additional Remark 1

A medical image processing device comprising: a medical image analysis processing unit that detects a notable region, which is a region to be notable, on the basis of the feature quantity of pixels of a medical image; and a medical image analysis result acquisition unit that acquires an analysis result of the medical image analysis processing unit.

Additional Remark 2

The medical image processing device comprising: a medical image analysis processing unit that detects presence or absence of an object to be notable, on the basis of the feature quantity of pixels of a medical image; and a medical image analysis result acquisition unit that acquires an analysis result of the medical image analysis processing unit.

Additional Remark 3

The medical image processing device, wherein the medical image analysis result acquisition unit acquires the analysis result from a recording device recording an analysis result of the medical image, and the analysis result includes any one or both of the notable region that is the region to be notable included in the medical image and presence or absence of the object to be notable.

Additional Remark 4

The medical image processing device, wherein the medical image is a normal light image that is obtained from the application of light in a white-light wavelength range or light in a plurality of wavelength ranges as the light in a white-light wavelength range.

Additional Remark 5

The medical image processing device, wherein the medical image is an image that is obtained from the application of light in a specific wavelength range, and the specific wavelength range is a range narrower than the white-light wavelength range.

Additional Remark 6

The medical image processing device, wherein the specific wavelength range is a blue-light wavelength range or a green-light wavelength range of a visible-light wavelength range.

Additional Remark 7

The medical image processing device, wherein the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

Additional Remark 8

The medical image processing device, wherein the specific wavelength range is a red-light wavelength range of a visible-light wavelength range.

Additional Remark 9

The medical image processing device, wherein the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

Additional Remark 10

The medical image processing device, wherein the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

Additional Remark 11

The medical image processing device, wherein the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

Additional Remark 12

The medical image processing device, wherein the medical image is an in-vivo image of the inside of a living body, and the in-vivo image includes information about the fluorescence of a fluorescent material present in the living body.

Additional Remark 13

The medical image processing device, wherein the fluorescence is obtained from the application of excitation light, which has a peak wavelength in a wavelength range of 390 nm to 470 nm, to the inside of the living body.

Additional Remark 14

The medical image processing device, wherein the medical image is an in-vivo image of the inside of a living body, and the specific wavelength range is an infrared wavelength range.

Additional Remark 15

The medical image processing device, wherein the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

Additional Remark 16

The medical image processing device, wherein a medical image acquisition unit comprises a special-light-image acquisition unit that acquires a special light image including information about the specific wavelength range on the basis of a normal light image obtained from the application of light in a white-light wavelength range or light in a plurality of wavelength ranges as the light in a white-light wavelength range, and the medical image is the special light image.

Additional Remark 17

The medical image processing device, wherein a signal in the specific wavelength range is obtained from an arithmetic operation based on color information about RGB or CMY included in the normal light image.

Additional Remark 18

The medical image processing device further comprising: a feature-quantity-image generation unit generating a feature quantity image from an arithmetic operation based on at least one of the normal light image that is obtained from the application of light in a white-light wavelength range or light in a plurality of wavelength ranges as the light in a white-light wavelength range and the special light image that is obtained from the application of light in a specific wavelength range, the medical image is the feature quantity image.

Additional Remark 19

An endoscope apparatus comprising: the medical image processing device according to any one of Additional remarks 1 to 18; and an endoscope that acquires an image from the application of at least one of light in a white-light wavelength range or light in the specific wavelength range.

Additional Remark 20

A diagnosis support apparatus comprising: the medical image processing device according to any one of Additional remarks 1 to 18.

Additional Remark 21

A medical service support apparatus comprising: the medical image processing device according to any one of Additional remarks 1 to 18.

The embodiment and other aspects of the invention have been described above, but the invention is not limited to the above-described aspects and can have various modifications without departing from the scope of the invention.

EXPLANATION OF REFERENCES

100: endoscope body
102: hand operation part
104: insertion part
106: universal cable
108: light guide connector
112: soft portion
114: bendable portion
116: hard distal end portion
116A: distal end-side end face
123: illumination unit
123A: illumination lens
123B: illumination lens
126: forceps port
130: imaging optical system
132: imaging lens
134: image pick-up element
136: drive circuit
138: AFE
170: light guide
200: processor
202: image input controller
204: image processing unit
204A: imaging timing setting unit
204B: imaging instruction receiving unit
204C: imaging control unit
204D: representative image storage unit
204E: neighboring image storage unit
204F: representative image display control unit
204G: representative image selection unit
204H: neighboring image display control unit
204I: region-of-interest detection unit
204J: switching instruction receiving unit
204K: image analysis unit
204L: designated image preservation unit
205: image input interface
206: video output unit
207: storage unit
207A: representative image
207B: neighboring image
207C: designated image
208: operation unit
209: voice processing unit
209A: speaker
210: CPU
211: ROM
212: RAM
300: light source device
310: light source
310A: visible light source
310B: infrared light source
330: stop
340: condenser lens
350: light source control unit
400: monitor
A01: button
A02: button
A03: button
A03a: button
A03c: slide bar
A04: button
A05: button
A06: button
A07: button
A08: button
A09: button
A10: button
A10a: button
A11: button
A12: button
A13: button
A14: button
A15: button
B01: button
B02: button B03: button
B04: button
B05: button
B06: button
B07: button
B08: button
B09: button
BT1: air/water supply button
BT2: suction button
BT3: function button
BT4: imaging button
C01: region
C02: region
C03: region
C04: region
C05: region
C06: region
C07: region
C08: region
C09: region
C10: region
C10a: region
C11: region
C12: region
C13: region
C14: region
C15: region
CB: checkbox
CR: cursor
FR: forceps
P1: indicator
P2: indicator
R1: display region
R2: display region
ROI: region of interest
S100 to S134: respective steps of diagnosis support method
T1: imaging period
V01: region
V02: region
V03: region
V04: region
V05: region
V06: region
V07: region
V08: region
V09: region
V10: region
V10a: region
V11: region
V12: region
V13: region
V14: region
V15: region
W1: window
W2: window
W3: window
i1: image
i2: image
i3: image
i4: image
i5: image
i6: image
i7: image
i8: image
i9: image
i10: image
iN1: neighboring image
iN2: neighboring image
iN3: neighboring image
iN4: neighboring image
iN5: neighboring image
iN6: neighboring image
iN7: neighboring image
iN8: neighboring image
iR1: representative image
iR2: representative image
iR2a: frame border
iR3: representative image
iR4: representative image
iR5: representative image
iR6: representative image

What is claimed is:

1. A diagnosis support system comprising:
an image sensor that captures a medical image according to an imaging instruction; and
a processor configured to:
  issue the imaging instruction to the image sensor to capture a plurality of medical images of which imaging times are different;
  store any of the plurality of medical images as representative images;
  store the plurality of medical images excluding the representative images as a plurality of groups of neighboring images such that each the plurality of groups of neighboring images are associated with the representative images;
  display the representative images in a list on a display device;
  receive a first selection from the representative images displayed in the list;
  extract neighboring images for diagnosis, from among a group of neighboring images which is associated with a selected representative image, by analyzing the neighboring images on the basis of at least one of exposures when the image sensor captures the neighboring images, or shaking amounts when the image sensor captures the neighboring images; and
  display at least one of the extracted neighboring images for diagnosis on the display;
  receive a second selection to select a neighboring image among the extracted neighboring images for replacing the selected representative image;
  replace the selected representative image with the selected neighboring image; and
  attach the representative image, which is replaced with the selected neighboring image, to a template of a diagnostic report.

2. The diagnosis support system according to claim 1, wherein the processor is configured to set an imaging timing on the basis of an input of a user's instruction and issues the imaging instruction to the image sensor according to the imaging timing.

3. The diagnosis support system according to claim 1, wherein the processor is configured to detect a region of interest from the medical image and issue the imaging instruction to the image sensor according to the detection of the region of interest.

4. The diagnosis support system according to claim 2, wherein the processor is configured to detect a region of interest from the medical image and issue the imaging instruction to the image sensor according to the detection of the region of interest.

5. The diagnosis support system according to claim 3, wherein the processor s configured to display the representative images in the list on the display device according to the detection of the region of interest.

6. The diagnosis support system according to claim 4, wherein the processor is configured to display the representative images in the list on the display device according to the detection of the region of interest.

7. The diagnosis support system according to claim 1, wherein the processor is configured to receive an imaging instruction operation from a user and issue the imaging instruction to the image sensor according to the imaging instruction operation.

8. The diagnosis support system according to claim 1, wherein each the plurality of group of neighboring images includes a medical image of which an imaging time is earlier than an imaging time of the representative image associated with each the plurality of group of neighboring images and a medical image of which a imaging time is later than the imaging time of the representative image associated with each the plurality of group of neighboring images.

9. The diagnosis support system according to claim 1, wherein the processor is configured to receive a switching instruction for switching a neighboring image being displayed on the display device to display an other neighboring image, according to the switching instruction, wherein the neighboring image and the other neighboring image are in the group of neighboring images.

10. The diagnosis support system according to claim 1, wherein processor is configured to switch and display the neighboring images in the group of neighboring images which is associated with the selected representative image on the display device until a switching stopping instruction is received, and continue to display, on the display device, a neighboring image which is being displayed when the switching stopping instruction is received.

11. The diagnosis support system according to claim 1, wherein the processor is configured to display the at least one of the extracted neighboring images in a display form different from a display form of the representative image.

12. The diagnosis support system according to claim 11, wherein the processor is configured to change at least one of a display position, a display window, or a display size of the at least one of the extracted neighboring images to be different from the representative image.

13. The diagnosis support system according to claim 11, wherein the processor is configured to change the display form of the at least one of the extracted neighboring images on the basis of a user's instruction.

14. The diagnosis support system according to claim 1, wherein the processor is configured to display the selected representative image to be distinguishable from the other representative images.

15. The diagnosis support system according to claim 1, wherein the processor is configured to preserve an image designated from among the representative images displayed in the list and the at least one of the extracted neighboring images.

16. An endoscope system comprising:
the diagnosis support system according to claim 1;
the display device; and
an endoscope including
an insertion part that is to be inserted into an object to be examined, and includes a hard distal end portion, a bendable portion connected to a proximal end side of the hard distal end portion, and a soft portion connected to a proximal end side of the bendable portion, and
an operation part connected to a proximal end side of the insertion part,
wherein the image sensor includes an imaging lens for forming an optical image of a subject, and an image pick-up element on which the optical image is formed by the imaging lens, and
the imaging lens is provided on the hard distal end portion.

17. A diagnosis support method by a diagnosis support system comprising an image sensor that captures a medical image according to an imaging instruction and a display device that displays the captured medical image, the diagnosis support method comprising:
issuing the imaging instruction to the image sensor to capture a plurality of medical images of which imaging times are different;
storing any of the plurality of medical images as representative images;
storing the plurality of medical images excluding the representative images as a plurality of groups of neighboring images such that each the plurality of groups of neighboring images are associated with the representative images;
displaying the representative images in a list on a display device;
receiving a first selection from the representative images displayed in the list;
extracting neighboring images for diagnosis, from among a group of neighboring images which is associated with a selected representative image, by analyzing the neighboring images on the basis of at least one of exposures when the image sensor captures the neighboring images, or shaking amounts when the image sensor captures the neighboring images;
displaying at least one of the extracted neighboring images for diagnosis on the display;
receiving a second selection to select a neighboring image among the extracted neighboring images for replacing the selected representative image;
replacing the selected representative image with the selected neighboring image; and
attaching the representative image, which is replaced with the selected neighboring image, to a template of a diagnostic report.

* * * * *